United States Patent [19]
Unger et al.

[11] Patent Number: 6,010,682
[45] Date of Patent: Jan. 4, 2000

[54] LIPOSOLUBLE COMPOUNDS USEFUL AS MAGNETIC RESONANCE IMAGING AGENTS

[75] Inventors: Evan C. Unger; DeKang Shen, both of Tucson, Ariz.

[73] Assignee: ImaRx Pharmaceuticals Corp., Tucson, Ariz.

[21] Appl. No.: 09/007,611

[22] Filed: Jan. 15, 1998

Related U.S. Application Data

[62] Division of application No. 08/762,367, Dec. 9, 1996, Pat. No. 5,762,910, which is a division of application No. 08/487,287, Jun. 7, 1995, Pat. No. 5,624,662, which is a division of application No. 08/173,649, Dec. 27, 1993, Pat. No. 5,466,438, which is a division of application No. 07/887,290, May 22, 1992, Pat. No. 5,312,617, which is a continuation-in-part of application No. 07/704,542, May 23, 1991, abandoned.

[51] Int. Cl.$^7$ ..................................................... A61B 5/055
[52] U.S. Cl. ................................. 424/9.361; 424/9.363; 514/184; 514/836; 540/465; 540/474
[58] Field of Search ...................................... 540/465, 474; 424/9.363, 9.361; 514/184, 836; 436/173; 600/420

[56] References Cited

U.S. PATENT DOCUMENTS

| | | | |
|---|---|---|---|
| 4,647,447 | 3/1987 | Gries et al. | 424/9 |
| 4,678,667 | 7/1987 | Meares et al. | 424/1.53 |
| 4,687,658 | 8/1987 | Quay | 424/9 |
| 4,687,659 | 8/1987 | Quay | 424/9 |
| 4,728,575 | 3/1988 | Gamble et al. | 428/402.2 |
| 4,730,066 | 3/1988 | White | 556/50 |
| 4,746,507 | 5/1988 | Quay | 424/9 |
| 4,804,529 | 2/1989 | Bardy et al. | 424/9.321 |
| 4,826,673 | 5/1989 | Dean et al. | 424/9 |
| 4,885,363 | 12/1989 | Tweedle et al. | 540/465 |
| 4,916,246 | 4/1990 | Felder et al. | 556/1 |
| 4,933,456 | 6/1990 | Rocklage et al. | 546/5 |
| 4,935,518 | 6/1990 | Rocklage et al. | 546/6 |
| 4,952,289 | 8/1990 | Ciccone et al. | 204/129 |
| 4,957,939 | 9/1990 | Gries et al. | 514/492 |
| 4,963,344 | 10/1990 | Gries et al. | 424/9 |
| 4,978,763 | 12/1990 | Rocklage et al. | 556/50 |
| 4,980,148 | 12/1990 | Dean | 424/9 |
| 4,983,376 | 1/1991 | Sherry | 424/9.363 |
| 4,994,259 | 2/1991 | Rocklage et al. | 424/9.361 |
| 5,011,925 | 4/1991 | Rajagopalan et al. | 544/58.1 |
| 5,078,986 | 1/1992 | Bosworth et al. | 424/9 |
| 5,318,771 | 6/1994 | Lauffer et al. | 424/9.361 |
| 5,330,743 | 7/1994 | Gibby et al. | 424/9 |
| 5,399,340 | 3/1995 | Radüchel et al. | 424/9 |
| 5,417,960 | 5/1995 | Schaefer et al. | 424/9.363 |
| 5,439,668 | 8/1995 | Almen et al. | 424/9.361 |
| 5,645,818 | 7/1997 | Jackels et al. | 424/9.363 |

FOREIGN PATENT DOCUMENTS

| | | |
|---|---|---|
| 413405 | 2/1991 | European Pat. Off. . |
| 3633245 | 3/1988 | Germany . |
| 3633246 | 3/1988 | Germany . |

OTHER PUBLICATIONS

Andress, Jr., "Symposium on Additives for Lubricants and Fuels Presented Before the Division of Petroleum chemistry, Inc.", 1973, *Am. Chem Soc.*, 18, 687–692.

Banker, G. and Rhodes, C. (Eds.), "Parenteral Products", *Modern Pharmaceutics*, 1990, 505–507, Marcel Dekker, Inc.

Erne, et al., "Lipophilic Amides of EDTA, NTA and Iminodiacetic Acid as Ionophores for Alkaline Earth Metal Cations", *Helv. Chim. Acta.*, 1980, 63, 2264–2270.

Kabalka, et al., "Gadolinium–Labeled Liposomes Containing Paramagnetic Amphipathic Agent: Targeted MRI Contrast Agents for the Liver", *Magnetic Resonance in Medicine*, 1988, 8, 89–95.

Kabalka, et al., "Gadolinium–Labeled Liposomes: Targeted MR Contrast Agents for the Liver and Spleen[1]", *Radiology*, 1987, 163, 255–258.

Navon, et al., "Liposomes Containing Paramagnetic Macromolecules as MRI Contrast Agents", *Magnetic Resonance in Medicine*, 1986, 3, 876–880.

Schwendener, et al., "A Pharmacokinetic and MRI Study of Unilamellar Gadolinium–, Manganese–, and Iron–DTPA–Stearate Liposmes as Organ–Specific Contrast Agents", *Investigative Radiology*, 1990, 25, 922–932.

Ulsperger and Dehns, "Additionsprodukte aus n–Fettaminen der Kettenlange $C_8$–$C_{12}$ und Glycid", *Journal fu praktische Chemie*, 1965 , 4, 195–212 Reihe, Band 27.

Unger, et al., "Liposomes as MR Contrast Agents: Pros and Cons", *Magnetic Resonance in Medicine*, 1991, 22, 304–308.

*Primary Examiner*—Gary E. Hollinden
*Attorney, Agent, or Firm*—Woodcock Washburn Kurtz Mackiewicz & Norris LLP

[57] ABSTRACT

Novel complexes of paramagnetic ions and compounds bearing long acyl chains have been synthesized as magnetic resonance imaging contrast agents. These novel liposoluble contrast agents may be administered alone, or with lipids, suspending agents or other additives. The lipids may be in the form of liposomes, micelles or lipid emulsions. The contrast agents of the invention have particular use in magnetic resonance imaging of the liver, blood pool and reticuloendothelial system.

70 Claims, No Drawings

LIPOSOLUBLE COMPOUNDS USEFUL AS MAGNETIC RESONANCE IMAGING AGENTS

CROSS-REFERENCE TO RELATED APPLICATIONS

This application is a division of U.S. application Ser. No. 08/762,367, filed Dec. 9, 1996, now U.S. Pat. No. 5,762,910, which is a division of U.S. application Ser. No. 08/487,287, filed Jun. 7, 1995, now U.S. Pat. No. 5,624,662, which is a division of U.S. application Ser. No. 08/173,649, filed Dec. 27, 1993, now U.S. Pat. No. 5,466,438, which is a division of U.S. application Ser. No. 07/887,290, filed May 22, 1992, now U.S. Pat. No. 5,312,617, which is a continuation-in-part of U.S. application Ser. No. 07/704,542, filed May 23, 1991, now abandoned. The disclosures of each of the foregoing applications are hereby incorporated herein by reference, in their entirety.

BACKGROUND OF THE INVENTION

Complexes of paramagnetic ions such as gadolinium-DTPA (Gd-DTPA) have been developed as magnetic resonance (MR) contrast agents. While gadolinium is quite toxic alone, the ion complex, Gd-DTPA, has much less toxicity, and has been used in MR imaging. Gd-DTPA, however, has limited use as an imaging agent. Indeed, while Gd-DTPA functions effectively as a contrast agent in the imaging of extracellular spaces, it provides little contrast enhancing effect as a blood pool imaging agent. Investigators have looked to other paramagnetic ions, such as manganese, for the development of similar complexes, such as Mn-DTPA. Such complexes, however, have been largely unstable in the serum, and thus suffer limitations similar to Gd-DTPA. Recently manganese pyridoxal phosphate compounds have been developed as an MR contrast agent. These compounds appear to function effectively as liver imaging agents, but are not thought to have much use as blood pool agents, or for other uses, such as agents for imaging the bone marrow, spleen or lymph nodes.

Liposomes have also been studied as MR contrast agents. Liposomal paramagnetic contrast agents have been shown to be effective in imaging the blood pool, liver, spleen and bone marrow. It has also been shown that small liposomes under 50 nm in size were more effective as MR contrast agents than larger liposomes, when the liposomes were used to entrap paramagnetic complexes such as Gd-DTPA. Even in the case of using small liposomes, however, the entrapped Gd-DTPA has less relaxivity than Gd-DTPA which is free in solution and not entrapped within liposomes. Gd-DTPA entrapped within a lipid membrane has a reduction in relaxivity because of the reduction in water flux that occurs across the intervening lipid bilayer. To improve the relaxivity workers have developed membrane bound paramagnetic ions but these have largely been unstable and usually do not show improved relaxivity.

The need is great for new and/or better contrast agents for magnetic resonance imaging. The present invention, which provides a new class of liposoluble compounds having characteristics such as improved relaxivity and/or high stability, is directed to these important ends.

SUMMARY OF THE INVENTION

The present invention is directed to contrast agents useful in magnetic resonance imaging.

Specifically, in one embodiment, the present invention pertains to contrast agents for magnetic resonance imaging comprising a paramagnetic ion in combination with a compound of the formula

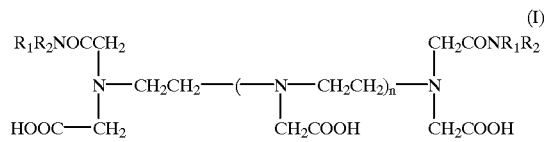

wherein:
each $R_1$ is, independently, a substituted or unsubstituted $C_7-C_{30}$ straight chain or cyclic compound;
each $R_2$ is, independently, a substituted or unsubstituted $C_1-C_{30}$, straight chain or cyclic compound which may be internally interrupted by O, NH, $NR_3$, or S, where $R_3$ is a $C_1-C_3$ alkyl; and
n is 0 to 1.

In another embodiment, the invention pertains to contrast agents for magnetic resonance imaging comprising a paramagnetic ion in combination with a compound of the formula

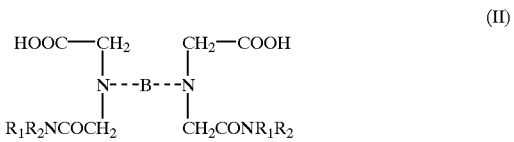

wherein:
each $R_1$ is, independently, a substituted or unsubstituted $C_7-C_{30}$ straight chain or cyclic compound;
each $R_2$ is, independently, a substituted or unsubstituted $C_1-C_{30}$ straight chain or cyclic compound which may be internally interrupted by O, NH, $NR_3$, or S, where $R_3$ is a $C_1-C_3$ alkyl; and
B is a substituted or unsubstituted $C_1-C_{30}$ straight chain or cyclic compound which may be internally interrupted by O, NH, $NR_3$, or S.

Moreover, the subject invention encompasses contrast agents for magnetic resonance imaging comprising a paramagnetic ion in combination with a compound of the formula

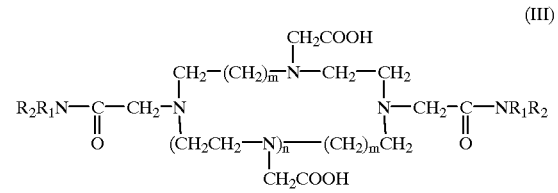

wherein:
each $R_1$ is, independently, a substituted or unsubstituted $C_7-C_{30}$ straight chain or cyclic compound;
each $R_2$ is, independently, a substituted or unsubstituted $C_1-C_{30}$ straight chain or cyclic compound which may be internally interrupted by O, NH, $NR_3$, or S, where $R_3$ is a $C_1-C_3$ alkyl;
each m is 1 to 2; and
n is 1 to 20.

Further, the invention contemplates contrast agents for magnetic resonance imaging comprising a paramagnetic ion in combination with a compound of the formula

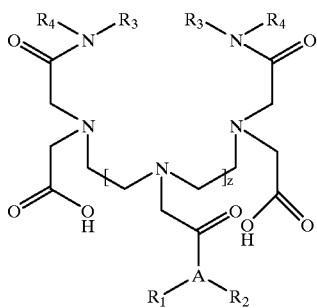

(IV)

wherein:

$R_1$ and $R_2$ are, independently, H, or a substituted or unsubstituted $C_7$–$C_{30}$ straight chain or cyclic compound;

each $R_3$ and $R_4$ are, independently, H, or a substituted or unsubstituted $C_1$–$C_{30}$ straight chain or cyclic compound which may be internally interrupted by O, NH, $NR_5$, or S, where $R_5$ is a $C_1$–$C_3$ alky; and A is N, or a N-containing substituted or unsubstituted $C_1$–$C_{30}$ straight chain or cyclic compound which may also be internally interrupted by O, NH, $NR_5$, or S, where $R_5$ is a $C_1$–$C_3$ alkyl;

z is 1 to 10;

provided that at least one of $R_1$ and $R_2$ is other than H, and at least one of $R_3$ and $R_4$ is other than H.

Still further, the invention provides a contrast agent for magnetic resonance imaging comprising a paramagnetic ion in combination with a compound of the formula

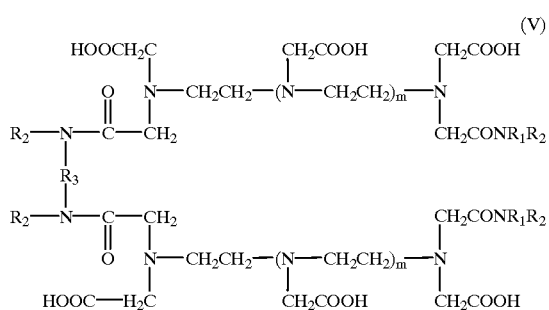

(V)

wherein:

each $R_1$ is, independently, a substituted or unsubstituted $C_7$–$C_{30}$ straight chain or cyclic compound;

each $R_2$ is, independently, a substituted or unsubstituted $C_1$–$C_{30}$ straight chain or cyclic compound which may be internally interrupted by O, NH, $NR_4$, or S, where $R_4$ is a $C_1$–$C_3$ alkyl;

$R_3$ is a substituted or unsubstituted $C_1$–$C_{30}$ straight chain or cyclic compound which may be internally interrupted by O, NH, $NR_4$, or S, where $R_4$ is a $C_1$–$C_3$ alkyl; and each m is, independently, 0 to 12.

Also encompassed in the subject invention are methods of providing an image of an internal region of a patient comprising (i) administering to the patient one or more of the foregoing contrast agents, and (ii) scanning the patient using magnetic resonance imaging to obtain visible images of the region, and methods for diagnosing the presence of diseased tissue in a patient comprising (i) administering to the patient one or more of the foregoing contrast agents, and (ii) scanning the patient using magnetic resonance imaging to obtain visible images of any diseased tissue in the patient.

These and other aspects of the invention will become more apparent from the present specification and claims.

DETAILED DESCRIPTION OF THE INVENTION

The invention is directed, in part, to a new class of contrast agents which are highly useful in, for example, magnetic resonance imaging. The new class of agents, which comprise paramagnetic ions complexed with novel acyl chain containing compounds, are described in more detail below.

Specifically, in one embodiment, the present invention pertains to contrast agents for magnetic resonance imaging comprising a paramagnetic ion in combination with a compound of the formula

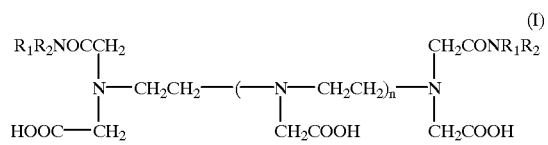

(I)

wherein:

each $R_1$ is, independently, a substituted or unsubstituted $C_7$–$C_{30}$ straight chain or cyclic compound;

each $R_2$ is, independently, a substituted or unsubstituted $C_1$–$C_{30}$ straight chain or cyclic compound which may be internally interrupted by O, NH, $NR_3$, or S, where $R_3$ is a $C_1$–$C_3$ alkyl; and n is 0 to 1.

In the above formula [I], $R_1$ may be a substituted or unsubstituted $C_7$–$C_{30}$ straight chain or cyclic compound. Preferably, $R_1$ is a $C_7$–$C_{24}$ more preferably a $C_8$–$C_{18}$, straight chain or cyclic compound. By straight chain compound, as used herein, it is meant an open chain compound, as, for example, an aliphatic compound, such as an alkyl, alkenyl or alkynyl compound. Preferably the straight chain compound is an alkyl, such as, for example, decyl, dodecyl, hexadecyl or octadecyl. By cyclic compound, as used herein, it is meant a closed chain compound (as in a ring of carbon atoms), as, for example, a cyclic aliphatic or aromatic compound. Exemplary cyclic compounds include phenylene, and steroids such as cholesterol, estrogen or testosterone. By substituted or unsubstituted, as used herein, it is meant that the compound may have any one of a variety of substituents, in replacement, for example, of one or more hydrogen atoms in the compound, or may have no substituents. Exemplary substitutents include $C_1$–$C_5$ alkyl and OH. Other suitable substituents will be readily apparent to one skilled in the art, once armed with the present disclosure. Particularly preferred compounds are those: wherein $R_1$ is an unsubstituted $C_7$–$C_{30}$ alkyl; wherein $R_1$ is an unsubstituted $C_8$–$C_{18}$ alkyl; wherein $R_1$ is decyl; wherein $R_1$ is dodecyl; and wherein $R_1$ is octadecyl.

In formula [I], $R_2$ is, independently, a substituted or unsubstituted $C_1$–$C_{30}$ straight chain or cyclic compound which may be internally interrupted by O, NH, $NR_3$, or S, where $R_3$ is a $C_1$–$C_3$ alkyl. Preferably, $R_2$ is a $C_2$–$C_{12}$, more preferably a $C_2$–$C_6$, straight chain or cyclic compound. Also preferably, the straight chain compound is an alkyl. By internally interrupted, as used herein, it is meant that the $C_1$–$C_{30}$ compound may have the carbon chain interrupted, as appropriate, with heteroatoms such as O, NH, $NR_3$, or S. If desired, the carbon chain may have no heteroatoms. By way of example, $R_2$ may comprise a polyhydric alcohol, such as —$CH_2$—CHOH—$CH_2OH$, —$CH_2$—$(CHOH)_2$—$CH_2OH$, —$CH_2$—$(CHOH)_3$—$CH_2OH$, —$CH_2$—$(CHOH)_4$—$CH_2OH$, or mannitol, sorbitol, glycidol, inositol, pentaerythritol, galacitol, adonitol, xylitol, alabitol. $R_2$ may also, for example, comprise a saccharide, including monosaccharides such as glucose, fructose, mannose, idose, galactose, allose, arabinose, gulose, fucose, erythrose, threose, ribose, xylose, lyxose, altrose, mannose, idose, talose, erythrulose, ribulose, xylulose, psicose, sorbose, tagatose, glucuronic acid, glucaric acid, galacturonic acid, manuronic acid, glucosamine, galactosamine and neuraminic acid, disaccharides such as sucrose, maltose, cellobiose, lactose, and trehalose, and polysaccharides such as a small starch molecules, as well as homo or heteropolymers of the aforementioned sugars. Additionally, $R_2$ may comprise, for example, an ether such as —$CH_2(CHOH)$n$CH_2OR_4$, where $R_4$ is —$(CH_2)$m-$CH_3$, m is 0 to 26, X is O, —NH—, $NR_3$, or S, or $R_2$ may comprise a saccharide ether. $R_2$ may also, for example, comprise —{$(CH_2)$—$(CH_2)$m-X}—$R_4$, —$(CH_2CH_2X)$m$R_4$ or —$(CHOH)$m-$OR_4$. Particularly preferred compounds are those: wherein $R_2$ is a $C_2$–$C_6$ alkyl; wherein $R_2$ is an uninterrupted $C_2$–$C_6$ alkyl which is substituted by OH; wherein $R_2$ is an unsubstituted $C_2$–$C_6$ alkyl which is internally interrupted by O.

Most preferred formula [I] compounds are those: wherein $R_1$ is octadecyl, $R_2$ is 2,3-dihydroxypropyl, and n is 0; wherein $R_1$ is decyl, $R_2$ is 2,3-dihydroxypropyl, and n is 0; wherein $R_1$ is dodecyl, $R_2$ is 2,3-dihydroxypropyl, and n is 0; wherein $R_1$ is octadecyl, $R_2$ is 2,3-dihydroxypropyl, and n is 1.

In another embodiment, the invention is directed to a contrast agent for magnetic resonance imaging comprising a paramagnetic ion in combination with a compound of the formula

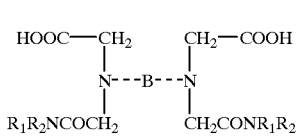

wherein:
each $R_1$ is, independently, a substituted or unsubstituted $C_7$–$C_{30}$ straight chain or cyclic compound;
each $R_2$ is, independently, a substituted or unsubstituted $C_1$–$C_{30}$ straight chain or cyclic compound which may be internally interrupted by O, NH, $NR_3$, or S, where $R_3$ is a $C_1$–$C_3$ alkyl; and
B is a substituted or unsubstituted $C_1$–$C_{30}$ straight chain or cyclic compound which may be internally interrupted by O, NH, $NR_3$, or S.

In formula [II], $R_1$ and $R_2$ are as described in connection with the formula [I] compounds.

B is a substituted or unsubstituted $C_1$–$C_{30}$ straight chain or cyclic compound which may be internally interrupted by O, NH, $NR_3$, or S, where $R_3$ is a $C_1$–$C_3$ alkyl. Particularly preferred compounds are those: wherein B is an unsubstituted and uninterrupted $C_3$–$C_{30}$ cycloalkyl or aromatic; or wherein B is an unsubstituted and uninterrupted $C_3$–$C_6$ cycloalkyl or aromatic. By way of example, B may be cyclohexane, phenylene, or —$CH_2CH_2X$—$(CH_2CH_2Y)$n-$CH_2CH_2$—, where X and Y, independently, are O, —NH—, $NR_3$, or S.

A most preferred formula [II] compound is the compound: wherein $R_1$ is octadecyl, $R_2$ is 2,3-dihydroxypropyl, and B is cyclohexyl.

The invention also contemplates a contrast agent for magnetic resonance imaging comprising a paramagnetic ion in combination with a polyazacyclic compound of the formula

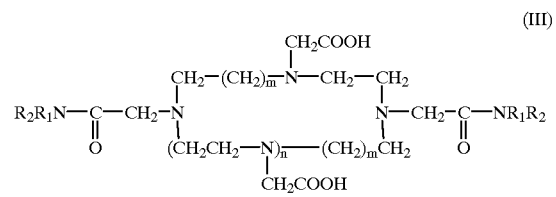

wherein:
each $R_1$ is, independently, a substituted or unsubstituted $C_7$–$C_{30}$ straight chain or cyclic compound;
each $R_2$ is, independently, a substituted or unsubstituted $C_1$–$C_{30}$ straight chain or cyclic compound which may be internally interrupted by O, NH, $NR_3$, or S, where $R_3$ is a $C_1$–$C_3$ alkyl;
each m is 1 to 2; and
n is 1 to 20.

In formula [III], $R_1$ and $R_2$ are as described in connection with the formula [I] compounds.

In formula [III], n is 1 to 20. Preferably, n is 1 to 10, more preferably, 1 to 5, and most preferably 1 to 2.

Particularly preferred compounds are those: wherein $R_1$ is octadecyl, $R_2$ is 2,3-dihydroxypropyl, m is 1, and n is 1.

Compounds that bear the polyazacyclic ring structure of formula [III] include 1,4,8,11-tetraazacyclotetradecane, 1,4,7,10-tetraazacyclododecane, 1,4,7,10,13-pentaazacyclopentadecane.

Further, the invention contemplates contrast agents for magnetic resonance imaging comprising a paramagnetic ion in combination with a compound of the formula

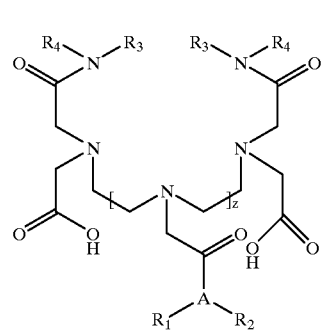

wherein:
$R_1$ and $R_2$ are, independently, H, or a substituted or unsubstituted $C_7$–$C_{30}$ straight chain or cyclic compound;
each $R_3$ and $R_4$ are, independently, H, or a substituted or unsubstituted $C_1$–$C_{30}$ straight chain or cyclic compound which may be internally interrupted by O, NH, $NR_5$, or S, where $R_5$ is a $C_1$–$C_3$ alkyl; and A is N, or a N-containing substituted or and trehalose, unsubstituted $C_1$–$C_{30}$ straight chain or cyclic compound which may also be internally interrupted by O, NH, $NR_5$, or S, where $R_5$ is a $C_1$–$C_3$ alkyl;

z is 1 to 10;

provided that at least one of $R_1$ and $R_2$ is other than H, and at least one of $R_3$ and $R_4$ is other than H.

In the above formula [IV], $R_1$ and $R_2$ may be H, or a substituted or unsubstituted $C_7$–$C_{30}$ straight chain or cyclic compound. Preferably, $R_1$ and $R_2$ are a $C_7$–$C_{24}$, more preferably a $C_8$–$C_{18}$, straight chain or cyclic compound. Exemplary cyclic compounds include phenylene, and steroids such as cholesterol, estrogen or testosterone. Preferably the straight chain compound is an alkyl. Particularly preferred compounds are those: wherein $R_1$ and $R_2$ are H, or an unsubstituted $C_7$–$C_{30}$ alkyl; wherein $R_1$ and $R_2$ are H, or an unsubstituted $C_8$–$C_{18}$ alkyl; and wherein $R_1$ and $R_2$ are H, or octadecyl.

In formula [IV], $R_3$ and $R_4$ are, independently, H, or a substituted or unsubstituted $C_1$–$C_{30}$ straight chain or cyclic compound which may be internally interrupted by O, NH, $NR_5$, or S, where $R_5$ is a $C_1$–$C_3$ alkyl. Preferably, $R_3$ and $R_4$ are a $C_2$–$C_{12}$, more preferably a $C_2$–$C_6$, straight chain or cyclic compound. Also preferably, the straight chain compound is an alkyl. By way of example, $R_3$ and $R_4$ may comprise a polyhydric alcohol, such as —$CH_2$—CHOH—$CH_2OH$, —$CH_2$—$(CHOH)_2$—$CH_2OH$, —$CH_2$—$(CHOH)_3$—$CH_2OH$, —$CH_2$—$(CHOH)_4$—$CH_2OH$, or mannitol, sorbitol, glycidol, inositol, pentaerythritol, galacitol, adonitol, xylitol, alabitol. $R_3$ and $R_4$ may also, for example, comprise a saccharide, including monosaccharides such as glucose, fructose, mannose, idose, galactose, allose, arabinose, gulose, fucose, erythrose, threose, ribose, xylose, lyxose, altrose, mannose, idose, talose, erythrulose, ribulose, xylulose, psicose, sorbose, tagatose, glucuronic acid, glucaric acid, galacturonic acid, manuronic acid, glucosamine, galactosamine and neuraminic acid, disaccharides such as sucrose, maltose, cellobiose, lactose, and trehalose, and polysaccharides such as a small starch molecules, as well as homo or heteropolymers of the aforementioned sugars. Additionally, $R_3$ and $R_4$ may comprise, for example, an ether such as —CH2(CHOH)nCH2O$R_6$, where $R_6$ is —$(CH_2)$m-$CH_3$, m is 0 to 26, preferably 0 to 10, more preferably 0 to 5, X is O, —NH—, $NR_5$, or S, or $R_3$ and $R_4$ may comprise a saccharide ether. $R_3$ and $R_4$ may also, for example, comprise —{$(CH_2)$—$(CH_2)$m-X}—$R_6$, —$(CH_2CH_2X)$m$R_6$, or —(CHOH)m-$O R_6$. Particularly preferred compounds are those: wherein $R_3$ and $R_4$ are H, or a $C_2$–$C_6$ alkyl; wherein $R_3$ and $R_4$ are H, or an uninterrupted $C_2$–$C_6$ alkyl which is substituted by OH; wherein $R_3$ and $R_4$ are H, or an unsubstituted $C_2$–$C_6$ alkyl which is internally interrupted by O.

In formula [IV], z is 1 to 10. Preferably, z is 1 to 5, more preferably 1 to 2.

A, in formula [IV] is N, or a N-containing substituted or unsubstituted $C_1$–$C_{30}$ straight chain or cyclic compound which may also be internally interrupted by O, NH, $NR_5$, or S, where $R_5$ is a $C_1$–$C_3$ alkyl. For example, A may be N, or A may be $R_7$—N—$R_7$, where each $R_7$ is, independently, —$(CH_2CH_2X)$n—, where n is 1 to 16, preferably 1 to 10, most preferably 1 to 2, and X is O, —NH—, $NR_3$, S or CHOH, where $R_3$ is a $C_1$–$C_3$ alkyl. A may also be a N-containing cyclic compound such as a pyrrole, pyrazole, imidazole, oxazole, thiazole, pyrroline, pyridine, pyrimidine, purine, quinoline, isoquinoline, or carbazole. Preferably, A is N or a N-containing $C_3$–$C_{30}$ cyclic compound. Most preferably, A is N.

A most preferred formula [IV] compound is that: wherein $R_1$ is octadecyl, $R_2$ is H, $R_3$ is methoxyethyl, $R_4$ is H, A is N, and z is 1.

In another aspect, the invention is directed to a contrast agent for magnetic resonance imaging comprising a paramagnetic ion in combination with a compound of the formula

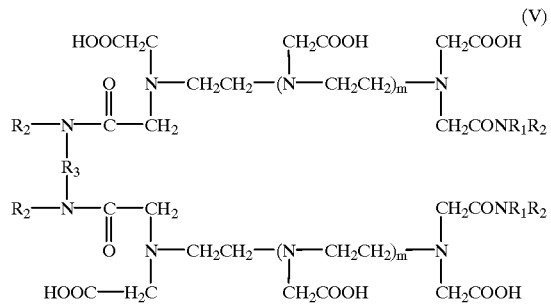

wherein:
each $R_1$ is, independently, a substituted or unsubstituted $C_7$–$C_{30}$ straight chain or cyclic compound;

each $R_2$ is, independently, a substituted or unsubstituted $C_1$–$C_{30}$ straight chain or cyclic compound which may be internally interrupted by O, NH, $NR_4$, or S, where $R_4$ is a $C_1$–$C_3$ alkyl;

$R_3$ is a substituted or unsubstituted $C_1$–$C_{30}$ straight chain or cyclic compound which may be internally interrupted by O, NH, $NR_4$, or S, where $R_4$ is a $C_1$–$C_3$ alkyl; and each m is, independently, 0 to 12.

In formula [V], $R_1$ and $R_2$ are as described in connection with the formula [I] compounds.

Also, in formula [V], $R_3$ is a substituted or unsubstituted $C_1$–$C_{30}$ straight chain or cyclic compound which may be internally interrupted by O, NH, $NR_4$, or S, where $R_4$ is a $C_1$–$C_3$ alkyl. Preferably, $R_3$ is a $C_2$–$C_{12}$, more preferably a $C_2$–$C_6$, straight chain or cyclic compound. Also preferably, the straight chain compound is an alkyl or alkenyl. By way of example, $R_3$ may be ethylene, propylene, butylene, etc. Also by way of example, $R_3$ may comprise a polyhydric alcohol, such as —$CH_2$—CHOH—$CH_2OH$, —$CH_2$—$(CHOH)_2$—$CH_2OH$, —$CH_2$—$(CHOH)_3$—$CH_2OH$, —$CH_2$—$(CHOH)_4$—$CH_2OH$, or mannitol, sorbitol, glycidol, inositol, pentaerythritol, galacitol, adonitol, xylitol, alabitol. $R_3$ may also, for example, comprise a saccharide, including monosaccharides such as glucose, fructose, mannose, idose, galactose, allose, arabinose, gulose, fucose, erythrose, threose, ribose, xylose, lyxose, altrose, mannose, idose, talose, erythrulose, ribulose, xylulose, psicose, sorbose, tagatose, glucuronic acid, glucaric acid, galacturonic acid, manuronic acid, glucosamine, galactosamine and neuraminic acid, disaccharides such as sucrose, maltose, cellobiose, lactose, and trehalose, and polysaccharides such as a small starch molecules, as well as homo or heteropolymers of the aforementioned sugars. Additionally, $R_3$ may comprise, for example, an ether such as —$CH_2(CHOH)$n$CH_2OR_5$, where $R_5$ is —$(CH_2)$n-$CH_3$, n is 0 to 26, X is O, —NH—, $NR_4$, or S, or $R_3$ may comprise a saccharide ether. $R_3$ may also, for example, comprise —{$(CH_2)$—$(CH_2)$n-X}—$R_5$, —$(CH_2CH_2X)$n$R_5$ or —(CHOH)n-$OR_5$. Other exemplary cyclic compounds include phenylene, and steroids such as cholesterol, estrogen or testosterone. Exemplary substitutents include $C_1$–$C_5$ alkyl and OH. Other suitable substituents will be readily apparent to one skilled in the art, once armed with the present disclosure. Particularly preferred formula [V] compounds are those: wherein $R_3$ is an unsubstituted $C_2$–$C_{12}$ alkyl or alkenyl; wherein $R_3$ is an unsubstituted $C_2$–$C_6$ alkyl or alkenyl; and wherein $R_3$ is ethylene. Other particularly preferred compounds are those: wherein $R_3$ is an uninterrupted $C_2$–$C_6$ alkyl or alkenyl which is substituted by OH; wherein $R_3$ is an unsubstituted $C_2$–$C_6$ alkyl or alkenyl which is internally interrupted by O.

In formula [V], m is 1 to 12. Preferably, m is 1 to 10, more preferably, 1 to 5, and most preferably 1 to 2.

A particularly preferred formula [V] compound is that: wherein $R_1$ is octadecyl, $R_2$ is 2,3-dihydroxypropyl, $R_3$ is ethylene, and m is 0.

The formula [V] compounds are extremely well suited to the chelation of multiple paramagnetic ions, including different types of ions.

As the above indicates, the length of the acyl chains covalently bound to the formula [I], [II], [III], [IV] and [V] compounds be varied up to 30 carbon atoms in length. Longer length chains, e.g. 18 carbon atoms, are preferred for use of the contrast agent with lipid compounds. Shorter carbon chains, e.g. 8 carbon atoms, are preferred when preparing the agents for use either alone or with suspending agents, generally because of their somewhat greater water solubility. Also, two acyl chains attached to the complex are preferred.

The liposoluble compounds of formulas [I], [II], [III], [IV] and [V] may be employed singly or in combination with one another, and in combination with one or more paramagnetic ions as contrast agents for magnetic resonance imaging. Exemplary paramagnetic ions include transition, lanthanide (rare earth) and actinide ions, as will be readily apparent to those skilled in the art, in view of the present disclosure. Preferable paramagnetic ions include those selected from the group consisting of $Cr^{+3}$, $Co^{+2}$, $Mn^{+2}$, $Ni^{+2}$, $Fe^{+3}$, $Fe^{+2}$, $La^{+3}$, $Cu^{+2}$, $Gd^{+3}$, $Ce^{+3}$, $Tb^{+3}$, $Pr^{+3}$, $Dy^{+3}$, $Nd^{+3}$, $Ho^{+3}$, $Pm^{+3}$, $Er^{+3}$, $Sm^{+3}$, $Tm^{+3}$, $Eu^{+3}$, $Yb^{+3}$ and $Lu^{+3}$. More preferably, the paramagnetic ion is selected from the group consisting of $Mn^{+2}$, $Fe^{+3}$ and $Gd^{+3}$, most preferably $Mn^{+2}$. If desired, two or more different ions may be used in combination. As those skilled in the art will recognize, once armed with the present disclosure, various combinations of the lipsoluble compounds and paramagnetic ions may be used to modify the relaxation behavior of the resulting contrast agent. The subject paramagnetic ion and liposoluble compound complexes of the invention have been found to be extremely effective contrast enhancement agents for magnetic resonance imaging.

The contrast agents of the invention may further comprise a lipid compound. Such lipid compounds may include any one of a variety of class or type of lipids, such as, for example, cholesterols, phosphatidylcholines, phosphatidylethanolamines, phosphatidylserines, phosphatidylglycerols, phosphatidic acids, phosphatidylinositols, phospholipids, lysolipids, fatty acids, sphingomyelin, glycosphingolipids, glucolipids, glycolipids, sulphatides, lipids with ether and ester-linked fatty acids and polymerizable lipids, and combinations thereof. The phospholipids are one generally preferred type of lipid, and include phospholipids, phosphatidylcholines, phosphatidylethanolamines, phosphatidylserines, phosphatidylglycerols, phosphatidic acids, phosphatidylinositols, diacetyl phosphates. One preferred type of phospholipid is a phosphatidyl choline lipid compound, such as egg phosphatidylcholine, dipalmitoyl phosphalidycholine, monomyristoyl phosphatidylcholine, monopalmitoyl phosphatidylcholine, monostearoyl phosphatidylcholine, monooleoyl phosphatidylcholine, dibutroyl phosphatidylcholine, divaleroyl phosphatidylcholine, dicaproyl phosphatidylcholine, diheptanoyl phosphatidylcholine, dicapryloyl phosphatidylcholine, distearoyl phosphatidylcholine, or other phosphatidyl compounds such as phosphatidylserine, phosphatidylinositol, and diphosphatidylglycerol. Another preferred lipid is a fatty acid lipid compound, such as linoleic acid, oleic acid, palmitic acid, linolenic acid, stearic acid, lauric acid, myristic acid, arachidic acid, palmitoleic acid, arachidonic acid ricinoleic acid, tuberculosteric acid, lactobacillic acid. A still other preferred lipid is a glycolipid compound such as cerebrosides, gangliosides (such as monosialoganglioside and GM1), and ceramides (such as lactosylceramide). A further preferred lipid is a ceramide which is ceramides As those skilled in the art will recognize, once placed in possession of the present invention, the lipids employed in the invention may be selected to optimize the particular diagnostic use, minimize toxicity and maximize shelf-life of the product. For example, neutral vesicles composed of phosphatidylcholine and cholesterol function quite well as intravascular contrast agents. To improve uptake by cells such as the reticuloendothelial system (RES), a negatively charged lipid such as phosphatidylglycerol, phosphatidylserine or similar material may be added. To prolong the blood pool half-life, highly saturated lipids that are in the gel state at physiological temperature such as dipalmitoyl phosphatidylcholine may be used. For even greater vesicle stability and prolongation of blood pool half-life the lipid can be polymerized using polymerizable lipids, or be coated with polymers such as polyethylene glycol so as to protect the lipid from serum proteins. In addition, gangliosides such as GM1 can be incorporated in the lipid.

The lipid compound employed in connection with the present invention may be in the form of a lipid emulsion, liposome, or micelle, or combinations thereof. Lipid emulsions, liposomes, and micelles, and methods for their preparation, are well known in the art.

For example, liposomes, that is, lipid vesicles comprising aqueous compartments enclosed by a lipid bilayer, may be prepared using any one of a variety of conventional liposome preparatory techniques which will be apparent to those skilled in the art. These techniques include freeze-thaw, as well as techniques such as sonication, chelate dialysis, homogenization, solvent infusion, micro-emulsification, spontaneous formation, solvent vaporization, reverse phase, French pressure cell technique, controlled detergent dialysis, and others, each involving preparing the liposomes in various fashions. Preparation may be carried out in a solution, such as a phosphate buffer solution, containing liposoluble contrast agents of the invention, so that the contrast agent is incorporated in to the liposome membrane. Alternatively, the contrast agents may be added to already formed liposomes. The size of the liposomes can be adjusted, if desired, by a variety of procedures including extrusion, filtration, sonication, homogenization, employing a laminar stream of a core of liquid introduced into an immiscible sheath of liquid, and similar methods, in order to modulate resultant liposomal biodistribution and clearance. Extrusion under pressure through pores of defined size is, however, the preferred means of adjusting the size of the liposomes. Although liposomes employed in the subject invention may be of any one of a variety of sizes, preferably the liposomes are small, that is, less than about 100 nm in outside diameter, more preferably less than about 50 nm. The foregoing techniques, as well as others, are discussed, for example, in U.S. Pat. No. 4,728,578; U.K. Patent Application GB 2193095 A; U.S. Pat. No. 4,728,575; U.S. Pat. No. 4,737,323; International Application PCT/US85/01161; Mayer et al., *Biochimica et Biophysica Acta*, Vol. 858, pp. 161–168 (1986); Hope et al., *Biochimica et Biophysica Acta*, Vol. 812, pp. 55–65 (1985); U.S. Pat. No. 4,533,254; Mayhew et al., *Methods in Enzymology*, Vol. 149, pp. 64–77 (1987); Mayhew et al., *Biochimica et Biophysica Acta*, Vol 755, pp. 169–74 (1984); Cheng et al, *Investigative Radiology*, Vol. 22, pp. 47–55 (1987); PCT/US89/05040, U.S. Pat. No. 4,162,282; U.S. Pat. No. 4,310,505; U.S. Pat. No. 4,921,706; and *Liposome Technology*, Gregoriadis, G., ed., Vol. I, pp. 29–31, 51–67 and 79–108 (CRC Press Inc., Boca Raton, Fla. 1984). The disclosures of each of the foregoing patents, publications and patent applications are incorporated by reference herein, in their entirety. Although any of a number of varying techniques can be employed, preferably the liposomes employed in the invention are prepared via microemulsification techniques, using, for example, a microfluidizer (Microfluidics, Newton, Mass.).

Micelles, that is, clusters or aggregates of lipid compounds, generally in the form of a lipid monolayer, may be prepared using any one of a variety of conventional liposome preparatory techniques which will be apparent to those skilled in the art. These techniques typically include the steps of suspension in an organic solvent, evaporation of the solvent, resuspension in an aqueous medium, sonication and then centrifugation. The foregoing techniques, as well as others, are discussed, for example, in Canfield et al., *Methods in Enzymology*, Vol. 189, pp. 418–422 (1990); El-Gorab et al, *Biochem. Biophys. Acta*, Vol. 306, pp. 58–66 (1973); *Colloidal Surfactant*, Shinoda, K., Nakagana, Tamamushi and Isejura, Academic Press, N.Y. (1963) (especially "The Formation of Micelles", Shinoda, Chapter 1, pp. 1–88); *Catalysis in Micellar and Macromolecular Systems*, Fendler and Fendler, Academic Press, N.Y. (1975). The disclosures of each of the foregoing publications are incorporated by reference herein, in their entirety.The micelles may be prepared in the presence of liposoluble contrast agents of the invention, or the contrast agent may be added to already formed micelles. Preferable lipid compounds used in preparing the micelles include, for example, monomyristoyl phosphatidylcholine, monopalmitoyl phosphatidylcholine, monostearoyl phosphatidylcholine, monooleoyl phosphatidylcholine, dibutroyl phosphatidylcholine, divaleroyl phosphatidylcholine, dicaproyl phosphatidylcholine, diheptanoyl phosphatidylcholine, dicapryloyl phosphatidylcholine. Other preferable lipid compounds for the micelles of the invention include, for example, linoleic acid, oleic acid, palmitic acid, linotenic acid, stearic acid, phosphatidylcholine, and phosphatidylethanolamine.

Lipid emulsions are also well known and may be prepared using conventional techniques. As those skilled in the art will recognize, a lipid emulsion is a substantially permanent heterogenous liquid mixture of two or more liquids that do not normally dissolve in each other, by mechanical agitation or by small amounts of additional substances known as emulsifiers. Typically, in preparing the emulsion, the lipids are added to ethanol or chloroform or any other suitable organic solvent and agitated by hand or mechanical techniques. The solvent is then evaporated from the mixture leaving a dried glaze of lipid. The lipids are resuspended in aqueous media, such as phosphate buffered saline, resulting in an emulsion. To achieve a more homogeneous size distribution of the emulsified lipids, the mixture may be sonicated using conventional sonication techniques, further emulsified using microfluidization (using, for example, a Microfluidizer, Newton, Mass.), and/or extruded under high pressure (such as, for example, 600 psi) using an Extruder Device (Lipex Biomembranes, Vancouver, Canada). Contrast agents of the invention may be added to the lipids during preparation of the emulsion, such as at the stage where the lipids are added to the organic solvent or at other stages of preparation, or may be added after the lipid emulsion has been formed, as desired. In preparing the lipid emulsions, particularly useful additives are, for example, soybean lecithin, glucose, Pluronic F-68, and D,L-α-tocopherol (Vitamin E), generally in an amount of about 0.03 to about 5 percent by weight. These additives are particularly useful where intravenous applications are desired. Techniques and ingredients for formulating lipid emulsions are well known in the art. Suitable procedures and emulsion ingredients are reported, for example, in *Modern Pharmaceutics*, pp. 505–507, Gilbert Baker and Christopher Rhodes, eds., Marcel Dekker Inc., New York, N.Y. (1990), the disclosures of which are hereby incorporated herein by reference in their entirety.

As those skilled in the art will recognize, any of the lipid compounds and preparations containing the lipid compounds (including the lipid and contrast agent preparations), may be lyophilized for storage, and reconstituted in, for example, an aqueous medium (such as sterile water or phosphate buffered saline), with the aid of vigorous agitation. In order to prevent agglutination or fusion of the lipids as a result of lyophilization, it may be useful to include additives in the formulation to prevent such fusion or agglutination. Additives which may be useful include sorbitol, mannitol, sodium chloride, glucose, trehalose, polyvinylpyrrolidone and polyethyleneglycol (such as PEG 400). These and other additives are described in the literature, such as in the U.S. Pharmacopeia, USP XXII, NF XVII, The United States Pharmacopeia, The National Formulary, United States Pharmacopeial Convention Inc., 12601 Twinbrook Parkway, Rockville, Md. 20852, the disclosures of which are hereby incorporated herein by reference in their entirety. Lyophilized preparations generally have the advantage of greater shelf life.

The contrast agent of the invention may further, if desired, comprise a suspending agent. Preferable suspending agents include polyethylene glycol, lactose, mannitol, sorbitol, ethyl alcohol, glycerin, lecithin, polyoxyethylene sorbitan monoleate, sorbitan monoleate and albumin. As those skilled in the art would recognize, various sugars and other polymers may also be employed, such as polyethylene, polyvinylpyrrolidone, propylene glycol, and polyoxyethylene. The amount of paramagnetic acylated MR contrast agent, e.g., Mn-DDP-EDTA, may vary from about 1 to 75 percent by weight of the total ingredients used to formulate the paramagnetic MR contrast agent emulsion.

The present invention is useful in imaging a patient generally, and/or in specifically diagnosing the presence of diseased tissue in a patient. The imaging process of the present invention may be carried out by administering a contrast medium of the invention to a patient, and then scanning the patient using magnetic resonance imaging to obtain visible images of an internal region of a patient and/or of any diseased tissue in that region. By region of a patient, it is meant the whole patient, or a particular area or portion of the patient. The contrast medium is particularly useful in providing images of the blood pool, liver, reticuloendothelial system, spleen, bone marrow, lymph nodes, and muscle. It is especially useful in imaging the blood pool, liver, reticuloendothelial system, spleen, particularly the blood pool. Because of their high relativity, these contrast agents are especially effective blood pool agents. Also, as shown by their in vivo effectiveness at low doses, these agents are highly effective at enhancing the liver and highly useful for improving the detection of hepatic metastases. The patient can be any type of animal, but preferably is a mammal, and most preferably a human.

Any of the various types of magnetic resonance imaging devices can be employed in the practice of the invention, the particular type or model of the device not being critical to the method of the invention. The magnetic resonance imaging techniques whch are employed are conventional and are described, for example, in Kean, D. M., and M. A. Smith, *Magnetic Resonance Imaging: Principles and Applications* (Williams and Wilkins, Baltimore 1986), the disclosures of which are hereby incorporated herein by reference in their entirety. Contemplated magnetic resonance imaging techniques include, but are not limited to, nuclear magnetic resonance (NMR), NMR spectroscopy, and electronic spin resonance (ESR). The preferred imaging modality is NMR.

As one skilled in the art would recognize, administration of the contrast agent to the patient may be carried out in various fashions, such as intravascularly, orally, rectally, etc., using a variety of dosage forms. Preferably, administration is by intravascularly. The useful dosage to be administered and the particular mode of administration will vary depending upon the age, weight and the particular animal and region thereof to be scanned, and the particular contrast agent of the invention to be employed. Typically, dosage is initiated at lower levels and increased until the desired contrast enhancement is achieved. By way of general guidance, typically between about 0.1 mg and about 1 g of the liposoluble compound of formulas [I], [II], [III], [IV], and [V], and between about 1 and about 50 micromoles of paramagnetic ion, each per kilogram of patient body weight, is administered, although higher and lower amounts can be employed. Similarly, by way of general guidance, where lipids or suspending agents are used in the formulation, generally between about 0.5 and about 50 percent by weight of the entire formulation of each may be employed, although higher and lower amounts may also be used.

In carrying out the method of the present invention, the contrast agent may be used alone, or in combination with other diagnostic, therapeutic or other agents. Such other agents include excipients such as flavoring or coloring materials.

In employing the contrast agents, they are preferably suspended in aqueous solution and the contrast medium formulated using sterile techniques. An advantage to using smaller liposomes (e.g., 100 nm and below in size) and micelles or emulsified lipids, as well as the simple suspension of paramagnetic ions and liposoluble compounds, is that the contrast agents may be filtered through 0.22 micron line filters either immediately prior to administration, such as by intravenous injection, or as a terminal step in formulation of the contrast agents, to remove any potential pyrogens.

For formulating these contrast agents into stable preparations other additives may be employed. For example, in formulating contrast agents for intravenous injection, parenteral additives may be included in the preparation. Such additives to include tonicity adjusting additives such as dextrose and sodium chloride, to formulate an isosmotic contrast medium. These tonicity additives are generally provided in minor amounts, such as about 0.1% to about 0.5% by weight of the total formulation. In addition, antimicrobial additives may be included in the final preparation so as to avoid bacterial growth. Such antimicrobial additives, in generally acceptable amounts, may include but are not limited to benzalkonium chloride (typically 0.01% by weight of the total formulation), benzyl alcohol (typically 1–2% by weight), chlorobutanol (typically 0.25–0.5% by weight), metacresol (typically 0.1–0.3% by weight), butyl p-hydroxybenzoate (typically 0.015% by weight), methyl p-hydroxybenzoate (typically 0.1–0.2% by weight), propyl p-hydroxybenzoate (typically 0.2% by weight), phenol (0.25–0.5% by weight) and thimerosal (typically 0.01% by weight). Additionally, antioxidants may be included in the preparation, and are particularly useful where the contrast agent contains unsaturated lipids. Such antioxidants in their generally useful amounts include ascorbic acid (typically 0.01–0.5% by weight), cysteine (typically 0.1–0.5% by weight), monothioglycerol (typically 0.1–1.0% by weight), sodium bisulfite (typically 0.1–1.0% by weight), sodium metabisulfite (typically 0.1–1.0% by weight), and tocopherols (typically 0.05–0.5% by weight). As those skilled in the art will recognize, the contrast agents of the invention may be formulated in a variety of means to be particularly suitable for intravascular delivery, delivery into any body cavity, or other delivery targets.

The contrast agents of the invention exhibit both high T1 and T2 relaxivity, especially high where lipids are also employed. Although not intending to be bound by any theory of operation, where lipid compounds are employed along with the liposoluble compounds and paramagnetic ions, it is believed that the high relaxivity of the subject contrast agents may be due to the liposoluble nature of the compounds, and, in part, the concomitant ability of those compounds to fix the contrast agent in the membranes of those lipid compounds. This, in turn, may serve to critically limit the tumbling of the contrast agents, thereby increasing relaxivity.

Another advantage of the present contrast agents are their stability. Indeed, not only does the increased stability result in a higher shelf life, but, more importantly, the stability of these compounds results in decreased toxicity. Unlike many of the contrast agent chelates in the prior art, the subject compounds are highly stable, even in media containing serum. As the examples show, the testing of stability in serum indicates that almost no metal ion dissociated from these novel contrast agents.

The present invention is further described in the following examples. In these example, Examples 1–8 and 10–17 are actual examples. Example 9 is a prophetic example. These examples are for illustrative purposes only, and are not to be construed as limiting the appended claims.

EXAMPLE 1

Synthesis of Manganese N,N'-Bis-(Carboxy-Octadecylamido-Methyl-N-2,3-Dihydroxypropyl)-Ethylenediamine-N,N'-Diacetate (Mn-EDTA-ODP) (Formula I, wherein $R_1$ is octadecyl, $R_2$ is 2,3-dihydroxypropyl, and n is 0)

Structure

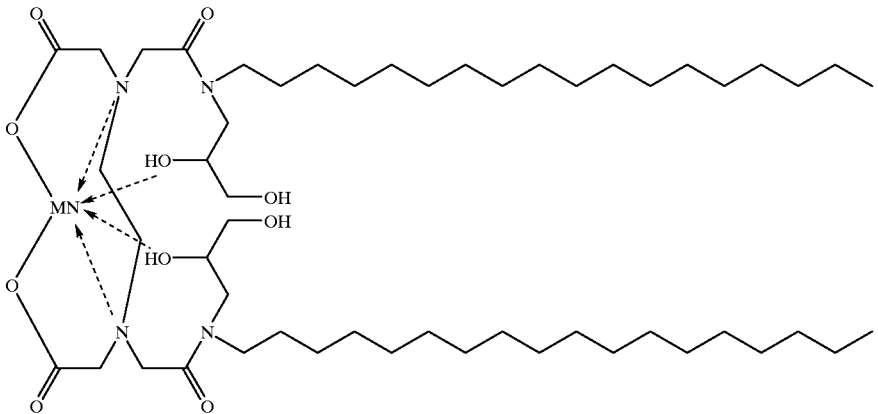

Synthetic Route (i) Synthesis of 3-Octadecylamino-1,2-Dihydroxy-Propane (ODP)

Octadecylamine (18 g) was dissolved in 200 ml methanol and heated to 60° C. Glycidol (4.95 g) was added dropwise under constant stirring over one and half hours. The reaction mixture was kept under reflux for one additional hour, and then cooled to room temperature, and evaporated to dryness, resulting in 22 g white solid material. This was then recrystallized from hexane, to yield ODP, mp 81–83° C.

(ii) Synthesis of N,N'-Bis(Carboxy-Octadecylamidomethylene-N-1,2,-Dihydroxypropyl)-Ethylenediamine N,N'-Diacetic Acid (EDTA-ODP)

EDTA anhydride (1.28 g) and 3-octadecylamino-1,2,-dihydroxypropane (3.43 g) were dissolved together in fresh dried methanol (160 ml). The reaction mixture was stirred at 35–40° C. for 12 hours, while the EDTA anhydride particles disappeared and the solution became transparent. The reaction mixture was then rotary evaporated to dryness and 4.6 g white solid was obtained, yielding EDTA-ODP, m.p. (decomposition) 130° C.

Elemental Analysis: $C_{52} H_{102} N_4 O_{10}$; Calc. C 66.20; H 10.90; N; 5.94; Anal. C 67.15; H 11.46; N; 5.90;

(iii) Synthesis of Manganese-N,N'-Bis(carboxy-Octadecylamidomethylene-N-1,2-Dihydroxypropyl)-Ethylenediamine N,N'-Diacetate (Mn-EDTA-ODP)

EDTA-ODP (0.942 g) was dissolved in 200 ml water. Manganese carbonate (0.115 g) was suspended in the reaction mixture and stirred overnight at 35° C. Carbon dioxide was released and the mixture was heated to 70° C. The reaction mixture became a soap-like solution, almost transparent. The reaction mixture was then rotary evaporated to dryness, and 1 g soap-like solid, Mn-EDTA-ODP, was obtained.

The compound prepared in Example 1 is as shown in the structure above. As one skilled in the art will recognize, once armed with the present disclosure, the 18 carbon moiety of the acyl chain may be altered, as desired, using conventional organic chemical techniques. By varying the number of carbon atoms in the acyl chains the solubility of the resulting acylated paramagnetic complex, as well as its in vivo biodistribution, may be altered.

EXAMPLE 2

Synthesis of Manganese N,N'-Bis-(Carboxy-Decylamidomethyl-N-2,3-Dihydroxypropyl)-Ethylenediamine-N,N'-Diacetate (Mn-EDTA-DDP) (Formula I, wherein $R_1$ is decyl and $R_2$ is 2,3-dihydroxypropyl, n is 0)

Structure

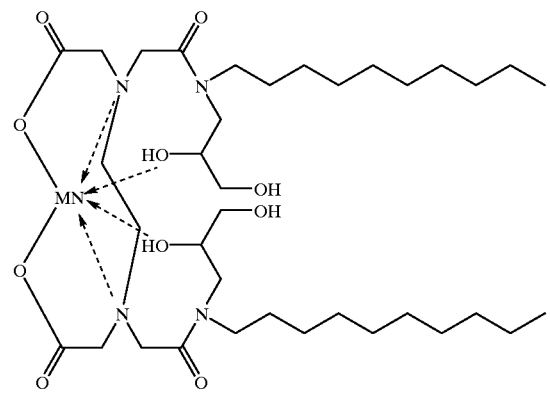

Synthetic Route (i) Synthesis of 3-Decylamino-1,2-Propanediol (DDP)

The procedures of Ulsperger et al., *J. Prakt. Chemie*, Vol. 27, pp. 195–212 (1965), the disclosures of which are hereby incorporated herein by reference in their entirety, were substantially followed. Specifically, 15.8 g decylamine (0.1 M) and 7.4 g glycidol (0.1 M) were mixed in 250 ml methanol at 60–80° C. and ref luxed for 10 hours. The methanol was rotary evaporatated. The product was a semisolid, 23.2 g (yield 100%). After recrystallization with hexane, pure white solid DDP, m.p. 65–67° C. (m.p.70–70.5° C., lit.), was recovered.

(ii) Synthesis of N,N'-Bis-(Carboxy-Decylamidomethyl-N-2,3-Dihydroxypropyl)-Ethylenediamine-N,N'-Diacetic Acid (EDTA-DDP)

EDTA anhydride 0.005 N (1.28 g) and DDP 0.01 M (2.31 g) were mixed together in 100 ml dried methanol. The reaction mixture was stirred at 35–40° C. for 12 hours, while the EDTA anhydride particles disappeared and the solution became transparent. The reaction mixture was then rotary evaporated to dryness, yielding 3.2 g (89%) of a white solid, EDTA-DDP.

Elemental Analysis: $C_{36} H_{70} N_4 O_{10}$; Calc. C 60.14; H 9.81; N 7.79; Anal. C 59.04; H 10.10; N 7.54.

(iii) Synthesis of Manganese N,N'-Bis-(Carboxy-Decylamidomethyl-N-2,3-Dihydroxypropyl)-Ethylenediamine-N,N'-Diacetic Acid (Mn-EDTA-DDP)

Manganese carbonate (0.23 g) and EDTA-DDP (1.44 g) were added to 100 ml water, and the reaction mixture stirred overnight at 40–45° C. Carbon dioxide was released, and the mixture was heated to 70° C., at which time the reaction mixture became a soap-like solution, almost transparent. This was rotary evaporated to dryness, and a soap-like solid, 1.39 g (89.8% yield) Mn-EDTA-DDP, was obtained.

EXAMPLE 3

Synthesis of Manganese N,N'-Bis-(Carboxy-Laurylamidomethyl-N-2,3-Dihydroxypropyl)-Ethylenediamine-N,N'-Diacetate (Mn-EDTA-LDP) (Formula I, wherein $R_1$ is dodecyl, $R_2$ is 2,3-dihydroxypropyl, and n is 0)

Structure

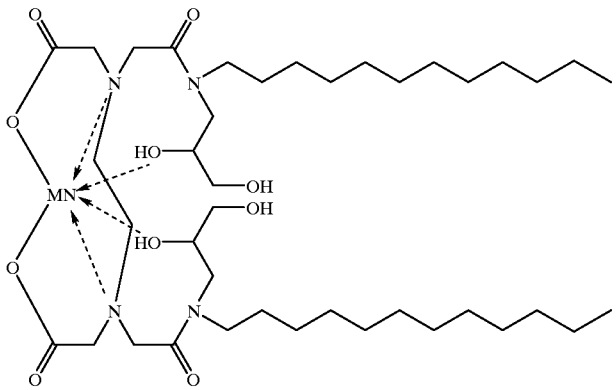

Synthetic Route (i) Synthesis of 3-Laurylamino-1,2-Dihydroxy-Propane (LDP)

The procedures of Ulsperger et al., *J. Prakt. Chemie*, Vol. 27, pp. 195–212 (1965), the disclosures of which are hereby incorporated herein by reference in their entirety, were substantially followed. Specifically, 18.54 g laurylamine (0.1 M) and 7.4 g glycidol (0.1 M) were mixed in 150 ml methanol at 60° C. for 5 hours. The mixture was refluxed for 1 hour at 70° C. The methanol was then removed by rotary evaporation. The product was a solid, 15.3 g (59% yield). After recrystallization from hexane, LDP, was recovered as a white crystal, m.p. 75–76° C. (m.p. 76–76.5° C., lit.).

(ii) Synthesis of N,N'-Bis-(Carboxy-Laurylamidomethyl-N-2,3-Dihydroxypropyl)-Ethylenediamine-N,N'-Diacetic Acid (EDTA-LDP)

EDTA anhydride (2.56 g; 0.01 M) and LDP (5.19 g; 0.02 M) were dissolved together in fresh dried methanol (160 ml). The reaction mixture was stirred at 35–40° C. for 12 hours, while the EDTA anhydride particles disappeared and the solution became transparent. The reaction mixture was then rotary evaporated to dryness and 7.75 g white solid was obtained (100% yield), of EDTA-LDP.

Elemental analysis: $C_{40} H_{78} N_4 O_{10}$; Calc. C: 61.99 H: 10.14 N: 7.23; Anal. C: 61.50 H: 10.18 N: 7.06.

(iii) Synthesis of Manganese N,N-Bis-(Carboxy-Laurylamidomethyl-N-2,3-Dihydroxypropyl)-Ethylenediamine-N,N'-Diacetate (Mn-EDTA-LDP)

Manganese carbonate (0.19 g; 0.0016 M) and EDTA-LDP (1.25 g; 0.0016 M) were added to 200 ml water, and the reaction mixture stirred overnight at 40° C. Carbon dioxide was released, and the mixture was heated to 70° C., at which time the reaction mixture became a soap-like solution, almost transparent. This was rotary evaporated to dryness, and 0.92 g of a soap-like solid, Mn-EDTA-LDP (yield 68.4%), was obtained.

EXAMPLE 4

Synthesis of Manganese N,N"-Bis-(Carboxyamidomethyl-N-2-Methoxyethylene)-N-Carboxy-Octadecylamidomethyl-Diethylenetriamine-N,N"-Diacetate (Mn-DTPA-OA) (Formula IV, wherein $R_1$ is octadecyl, $R_2$ is H, $R_3$ is 2-methoxyethyl, $R_4$ is H, A is N, and z is 1)

Structure

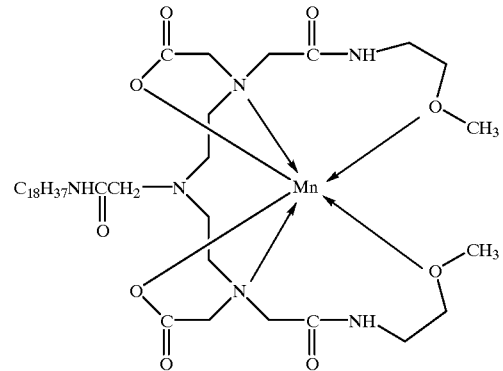

Synthetic Route (i) Synthesis of N,N"-Bis(Carboxyamidomethyl-N-(2-Methoxyethyl))-Diethylenetriamine-N,N',N"-Triacetic Acid (DTPA-MEA)

Diethylenetriamine-N,N',N"-triacetic acid (DTPA) (0.79 g) and fresh distilled 2-methoxyethylamine (0.3 g) were mixed in dried methanol (50 ml) and stirred overnight. The mixture became transparent. The methanol was then evaporated and 0.84 g of a white solid, DTPA-MEA, obtained.

(ii) Synthesis of N,N"-Bis-(Carboxyamidomethyl-N-2-Methoxyethylene)-N'-Carboxy-Octadecylamidomethyl-Diethylenetriamine-N, N"-Diacetic Acid (DTPA-OA-MEA)

Octadecylamine (0.807 g) and DTPA-MEA (1.296 g) were mixed together with N-dimethylforamide (DMF) (30 ml), and added dropwise to a solution of dicyclohexylcarbodiimide (DCC) in 5 ml DMF at 0–5° C., and stirred for 2 hours. The temperature was then raised to 40–45° C. for one additional hour, after which the reaction was completed. The DMF was then evaporated off under reduced pressure, the residue diluted with water, and the precipitate filtered out. The water was then evaporated under reduced pressure, yielding 1.5 g of a soap-like material, DTPA-OA-MEA.

(iii) Synthesis of Manganese N,N"-Nis-(Carboxyamidomethyl-N-2-Methoxyethylene)-N'-Carboxy-Octadecylamidomethyl-Diethylenetriamine-N, N"-Diacetate (Mn-DTPA-OA)

Manganese carbonate (0.25 g) and DTPA-OA-MEA (1.5 g) were mixed with 80 ml of water and stirred over night, resulting in a soap-like solution. Another portion of manganese carbonate (0.25 g) was then added and stirred overnight. The small amount of unreacted manganese carbonate was filtered off and the sample was evaporated using a rotary evaporator, yielding 1.86 g of a soap-like material, (Mn-DTPA-OA).

EXAMPLE 5

Gadolinium N,N"-Bis-(Carboxyoctadecylamidomethyl-N-2,3-Dihydroxypropyl)-Diethylenetriamine-N,N"-Triacetate (Gd-DTPA-ODP) (Formula I, wherein $R_1$ is octadecyl, $R_2$ is 2,3-dihydroxypropyl, n is 1)

Structure

Synthetic Route (i) Synthesis of N,N"-Bis-(Carboxyoctadecylamidomethyl-N-2,3-Dihydroxypropyl)-Diethylenetriamine-N,N',N"-Triacetic acid (ODP-DTPA)

ODP (3.43 g) was dissolved in 150 ml dried methanol and heated to 40° C. The anhydride of diethylenetriaminepentaacetic acid (DTPA) (1.79 g) was added by stirring, and the mixture stirred overnight. The solution became transparent. The solution was then evaporated and a white solid product, ODP-DTPA (5.2 g), obtained.

(ii) Synthesis of Gadolinium N,N"-Bis-(Carboxyoctadecylamidomethyl-N-2,3-Dihydroxypropyl)-Diethylenetriamine-N,N',N"-Triacetate (Gd-DTPA-ODP)

Gadolinium chloride (0.34 g) (containing 28.8% water) was dissolved in 20 ml of ethanol, mixed with one gram of ODP-DTPA in 20 ml of ethanol, stirred for 24 hours, and then evaporated to dryness. Ethanol (20 ml) was again added to the mixture, and the mixture again evaporated to dryness. This step was repeated three additional times, yielding 1.168 g of Gd-DTPA-ODP.

EXAMPLE 6

Synthesis of Ferric N,N"-Bis(Carboxyoctadecylamidomethyl-N-2,3-Dihydroxypropyl)-Diethylenetriamine-N,N',N"-Triacetate (Fe-DTPA-ODP) (Formula I, wherein $R_1$ is octadecyl, $R_2$ is 2,3-dihydroxypropyl, n is 1)

Structure

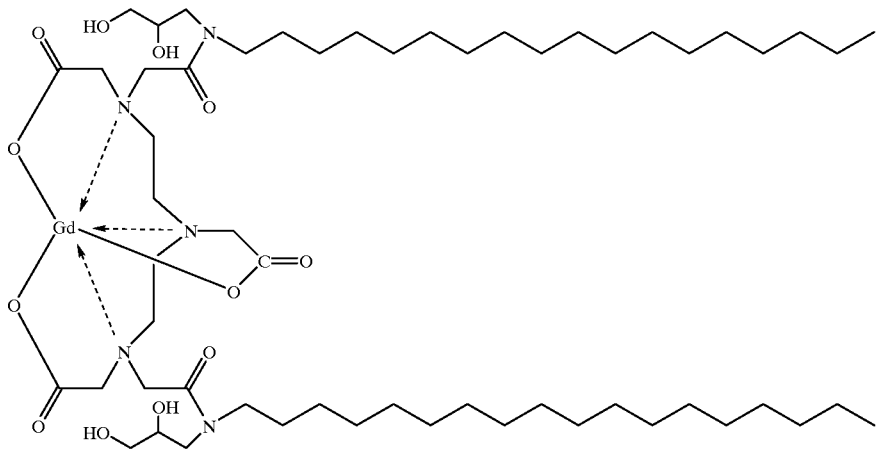

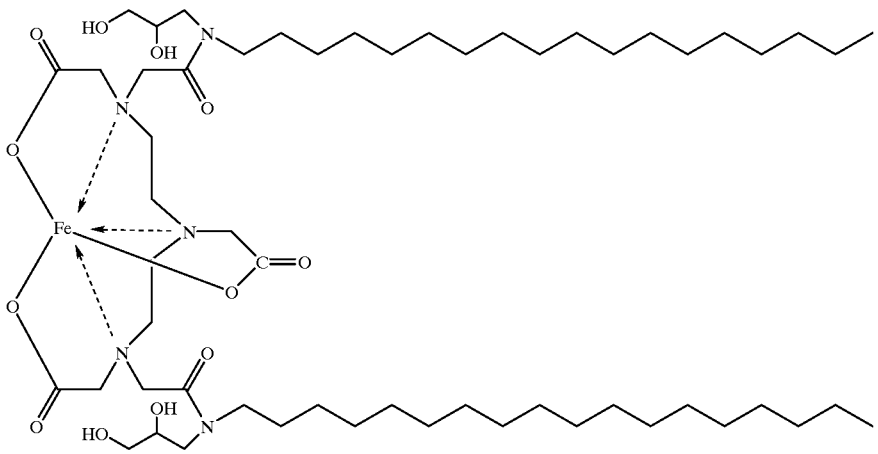

Synthetic Route

Synthesis of Ferric N,N"-Bis(Carboxyoctadecylamidomethyl-N-2,3-Dihydroxypropyl)-Diethylenetriamine-N,N',N"-Triacetate (Fe-DTPA-ODP)

Ferric chloride (0.16 g) was dissolved in 20 ml of ethanol and mixed with 1 g of ODP-DTPA in 20 ml of ethanol, stirred for 24 hours, and evaporated to dryness. To this was again added 20 ml of ethanol, and the mixture evaporated to dryness. This step was repeated an additional three times. A green-yellow solid of about 1 g, Fe-DTPA-ODP, was obtained.

EXAMPLE 7

Synthesis of Manganese 1,7-Bis-(Carboxy-Octadecylamidomethyl-N-2,3-Dihydroxypropyl)-1,4,7,10-Tetraazacyclododecane-4,10-Diacetate (Mn-DOTA-ODP) (Formula III, wherein $R_1$ is octadecyl, $R_2$ is 2,3-dihydroxypropyl, n is 1, and m is 1)

Structure

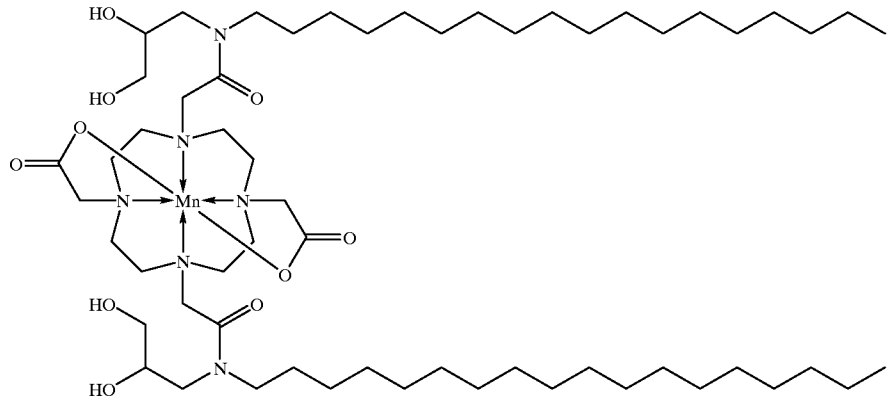

Synthetic Route (i) Synthesis of 1,4,7,10-Tetraazacyclododecane-1,4,7,10-Tetraacetic Acid (DOTA) Anhydride Two g of 1,4,7,10-tetraazacyclododecane-1,4,7,10-tetraacetic acid was mixed with 30 g of acetic anhydride and heated for eight hours. The reaction mixture was cooled down to room temperature and the precipitate filtered, resulting in DOTA anhydride.

(ii) Synthesis of 1,7,-Bis-(Carboxy-Octadecylamidomethyl-N-2,3-Dihydroxypropyl)-1,4,7,10-Tetraazacyclododecane-4,10-Diacetic acid (DOTA-ODP)

DOTA anhydride (0.74 g) and ODP (1.37 g) were mixed with 50 ml fresh dried methanol and stirred overnight. The reaction mixture became transparent. The methanol was then evaporated off, yielding a white solid, DOTA-ODP.

(iii) Synthesis of Manganese 1,7-Bis-(Carboxy-Octadecylamidomethyl-N-2,3-Dihydroxypropyl)-1,4,7,10-Tetraazacyclododecane-4,10-Diacetate (Mn-DOTA-ODP)

Manganese carbonate (0.115 g) and DOTA-ODP (1 g) were mixed together with 100 ml water and stirred for two hours, then heated to 40° C., and stirred for an additional two hours. The reaction mixture was evaporated, and a 1 g soaplike solid, Mn-DOTA-ODP, was obtained.

EXAMPLE 8

Preparation of Liposomal Mn-EDTA-ODP, Mn-DTPA-OA-MEA, Gd-DTPA-ODP, Mn-EDTA-DDP and Mn-EDTA-DDP Mn-EDTA-ODP was incorporated into small unilamellar liposomes as follows. Egg phosphatidylcholine (EPC) and cholesterol (8:2 molar ratio) were suspended in chloroform and a 33 percent molar concentration of Mn-EDTA-ODP was added to the solution. The chloroform was then evaporated under vacuum and the dried lipids and Mn-EDTA-ODP were resuspended in phosphate buffered saline (PBS).

The mixture was transferred to a cryovial, quench frozen in liquid nitrogen, and thawed five times. The material was then extruded through an extruder device (Lipex Biomembranes, Vancouver, B.C., Canada) 10 times using a 400 nm diameter pore size polycarbonate filter to produce 400 nm liposomes. A portion of the 400 nm liposomes were then extruded through 100 nm diameter filters 10 times to produce 100 nm liposomes. A portion of the 100 nm liposomes were then extruded 10 times through 15 nm filters, producing liposomes of 30 nm size. Previously, it was shown by quasi-elastic light scattering that such extrusions through 400 nm filters produces liposomes of about 400 nm size, through 100 nm filters produces liposomes of about 100 nm size, and through 15 nm filters produces liposomes of about 30 nm in size. In a similar fashion, 400 nm, 100 nm and 30 nm liposomal Mn-DTPA-OA-MEA, Gd-DTPA-ODP, Mn-EDTA-DDP and Mn-EDTA-DDP compounds were also prepared.

EXAMPLE 9

Intravenous lipid emulsions are formulated with a contrast agent of the invention to provide an emulsified preparation comprising the contrast agent of the invention following the techniques and using the ingredients described in *Modern Pharmaceutics*, pp. 505–507, Gilbert Baker and Christopher Rhodes, eds., Marcel Dekker Inc., New York, N.Y. (1990). Specifically, the following emulsions are prepared:

Example 9A: soybean oil 10%, egg phosphatidylcholine (EPC) 1.2%, glycerol 2.25%, 100 ml of water.

Example 9B: soybean oil 20%, EPC 1.2%, glycerol 2.25%, 100 ml of water.

Example 9C: soybean oil 5%, safflower oil 5%, EPC 1.2%, glycerol 2.5%, 100 ml water.

Example 9D: cottonseed oil 15%, soybean phospholipid 1.2%, and sorbitol 5%.

EXAMPLE 10

Synthesis of Bi-Mn-EDTA-DDP (LDP,ODP) (Formula V, wherein $R_1$ is octadecyl, $R_2$ is 2,3-dihydroxypropyl, $R_3$ is ethylene, and m is 0)

Structure

Synthetic Route (i) Synthesis of N,N' Di-s,3-Dihydroxypropyl-Ethylenedimine (Di-DPEA)

Ethylenediamine (6 g) was dissolved in methanol (70 ml), and heated to 60° C. Glycidol (14.8 g) diluted with methanol (30 ml), added dropwise into the boiling solution of ethylenediamine, for 45 minutes. The mixture was stirred and refluxed for two additional hours. The methanol was evaporated by a rotary evaporator, resulting in 20 g of Di-DPEA.

(ii) Synthesis of Bi-EDTA-DDP

Two grams Di-DPEA was dissolved in 30 ml dried methanol, added dropwise, and stirred thoroughly. Next, 5.1 g EDTA anhydride and 100 ml dried methanol was added to the mixture over one hour at room temperature, and the mixture continuously stirred for 3 hours at room temperature. DDP (4.7 g) was added into the reaction mixture, and the mixture stirred for four additional hours. The reaction temperature was then raised to 50° C., the mixture stirred for one hour, and the solvent evaporated, resulting in 11.4 g solid Bi-EDTA-DDP.

(iii) Synthesis of Bi-Mn-EDTA-DDP

Bi-EDTA-DDP (5.9 g) was dissolved in 100 ml water, and manganese carbonate (1.2 g) added. The mixture was stirred overnight, and then heated to 70° C. and stirred for an additional hour. The water was evaporated off, yielding 6 g Bi-Mn-EDTA-DDP.

As the structure shown above for Example 10 reveals, the compound Bi-Mn-EDTA-DDP contains a chelating unit that is able to chelate more than a single paramagnetic ion. Although this compound is shown chelating only two Mn ions, it may, if desired, be prepared to chelate more than one of paramagnetic ions in one molecule, for example, $Mn^{+2}$ and $Fe^{+2}$, $Gd^{+3}$ and $Fe^{+3}$, $Gd^{+3}$ and $Mn^{+2}$, and $Fe^{+3}$ and $Fe^{+2}$.

EXAMPLE 11

One gram of human serum albumin, obtained from pooled human serum, was mixed with 10 mg of EDTA-DDP in 10 cc of normal saline. The mixture was sonicated with a Heat Systems probe Sonicator (Heat Systems Probes, Farmingdale, N.Y.) at level 4 for 1 minute. The material was then cooled to 4° C. and, after 48 hours, 2.5 mg of $MnCl_2$ was added to the preparation. The preparation was then dialyzed against normal saline for 48 hours, generating Mn-EDTA-DDP suspended in (non-covalently bound to) albumin.

EXAMPLE 12

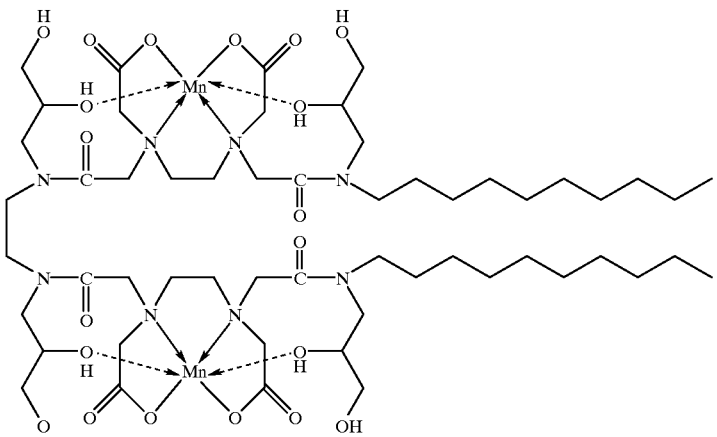

The procedures of Example 11 were substantially followed, except that instead of sonication, the albumin and Mn-EDTA-DDP were heated to a temperature of 100° C. for two minutes.

EXAMPLE 13

The procedures of Example 12 were substantially followed, except that the albumin and Mn-EDTA-DDP were heated to a temperature of 75° C. for 60 minutes.

EXAMPLE 14

Liposomes prepared in accordance with Example 8 incorporating Mn-EDTA-DDP in the membrane bilayer were subjected to a Microfluidizer (Microfluidics, Newton, Mass.). Specifically, the liposomes were passed 10 times through the microfluidizer at a pressure of 16,000 psi and a flow rate of 450 ml/minute. The resulting liposomes had a mean average size of 30–40 nm, which was verified by Quasi Elastic Light Scattering (QEL).

EXAMPLE 15

For comparison to contrast agents of the invention, solutions of manganese chloride and manganese chloride liposomes were prepared. Specifically, the $MnCl_2$ liposomes were prepared by resuspending dried lipids 8:2 EPC/cholesterol in an aqueous solution of manganese chloride. Different concentration solutions of $MnCl_2$ ranging from 10 to 500 millimolar manganese were used to make the $MnCl_2$ liposomes. Unentrapped manganese was removed by exhaustive dialysis.

EXAMPLE 16

Synthesis of Manganese N,N'-Bis-(Carboxy-Octadecylamidomethyl-N-2,3-Dihydroxypropyl)-Cyclohexane-1,2-Diamino-N,N'-Diacetate (Mn-CHTA-ODP) (Formula II, wherein $R_1$ is octadecyl, $R_2$ is 2,3-dihydroxypropyl, B is cyclohexyl)

Structure

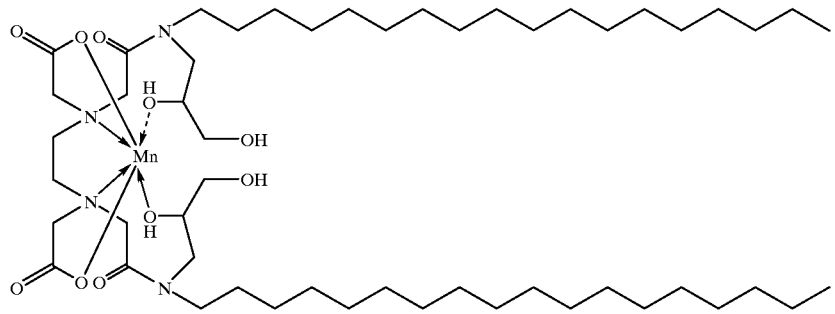

Synthetic Route
(i) Synthesis of Cyclohexane-1,2-Diamino-N,N,N',N'-Tetraacetic Acid (CHTA) Anydride Cyclohexane-1,2-diamino-N,N,N',N'-tetraacetic acid (3.46 g) was mixed with acetic anhydride (30 g), and heated for 8 hours. The reaction mixture was cooled to room temperature, and the precipitate filtered out, yielding cyclohexane-1,2-diamino-N,N,N',N'-tetraacetic acid anhydride.

(ii) Synthesis of N,N',-Bis-(Carboxy-Octadecylamidomethyl-N-2,3-Dihydroxypropyl)-Cyclohexane-1,2-Diamino-N,N'-Diaceticacid (CHTA-ODP)

CHTA anhydride (3.1 g) and ODP (6.86 g) was mixed with 100 ml fresh dried methanol, and stirred overnight. The reaction mixture became transparent. The methanol was then evaporated off, resulting in a white solid, CHTA-ODP.

(iii) Synthesis of Manganese N,N'-Bis-(Carboxy-Octadecylamidonlethyl-N-2,3-Dihydroxypropyl)-Cyclohexane-1,2-Diamino-N,N'-Diacetate (Mn-CHTA-ODP)

Manganese carbonate (0.6 g) and CHTA-ODP (5 g) was mixed together with 100 ml water, stirred for 2 hours, and then heated to 40° C. The mixture was stirred for an additional two hours, and the water evaporated, yielding 5 g of a soap like solid, Mn-CHTA-ODP.

EXAMPLE 17

In Vitro Relaxivity of Liposomal Mn-EDTA-ODP, Mn-DTPA-OA-MEA, Gd-DTPA-ODP, Mn-EDTA-DDP and Mn-EDTA-DDP Liposomal contrast agents of the invention, prepared in accordance with Example 8, were serially diluted from a stock solution of known concentration. Diluted concentrations for testing were held constant at 0.5 mM, 0.25 mM, 0.125 mM, 0.100 mM, 0.05 mM, and 0.025 mM, respectively. Samples were scanned on a Toshiba MRT 50A 0.5 Tesla (21.3 MHz) clincal magnet equipped with a QD head coil (Toshiba MRI scanner, Nasu, Japan). Signal intensities for resulting scans were then statistically analyzed using a computer curve fitting program (Fit All, MTR Software, version 1.1). Resulting relaxivities were regressed against the concentration to determine R1 (1/T1 mmol $sec^{-1}$) and $R_2$ (1/T1 mmol $sec^{-1}$). The results were compared with similar scans for other compounds not within the scope of the present invention. Specifically, as a comparison for the contrast agents of the invention, 0.5 Tesla scans were made of Gd-DTPA (no liposome), Mn-EDTA-MEA (no liposome), Mn-EDTA-MEA (incorporated into a liposome of 0.1 micron), and phosphate buffered saline (PBS).

The results are shown in Table I below. As shown in Table I, the contrast agents of the invention have excellent relaxivity. The relaxivity is greatest for the smallest (30 nm) liposomes containing Mn-EDTA-DDP.

TABLE I

| Relaxivity of Contrast Agents at 0.5 Tesla | | |
|---|---|---|
| Sample | R1 | R2 |
| PBS | 0.300 ± 0.30 | 0.395 ± 0.169 |
| Gd-DTPA | 4.68 ± 0.279 | 5.17 ± 0.148 |
| Mn-EDTA-MEA | 3.12 ± 0.124 | 5.61 ± 0.011 |
| Gd-DTPA-ODP liposomes 0.1 micron | 3.427 ± 0.141 | 4.190 ± 0.087 |
| Mn-EDTA-MEA liposomes 0.1 micron | 0.941 ± 0.045 | 1.12 ± 0.117 |
| Mn-DTPA-MEA-OA liposomes 0.4 micron | 1.216 ± 0.0827 | 1.631 ± 0.211 |
| Mn-EDTA-ODP liposomes 0.4 micron | 7.77 ± 0.742 | 11.44 ± 0.83 |
| Mn-EDTA-ODP liposomes 0.1 micron | 17.44 ± 0.97 | 23.6 ± 1.82 |
| Mn-EDTA-ODP liposomes 0.03 micron | 31.77 ± 1.99 | 35.0 ± 1.76 |
| Mn-EDTA-LDP liposomes 0.1 micron | 18.39 ± 0.231 | 22.46 ± 0.687 |
| Mn-EDTA-DDP liposomes 0.4 micron | 5.73 ± 0.195 | 7.22 ± 0.100 |

TABLE I-continued

Relaxivity of Contrast Agents at 0.5 Tesla

| Sample | R1 | R2 |
|---|---|---|
| Mn-EDTA-DDP liposomes 0.1 micron | 30.27 ± 1.15 | 36.69 ± 1.26 |
| Mn-EDTA-DDP liposomes 0.03 micron | 37.4 ± 1.12 | 53.2 ± 0.228 |

In all liposome examples in Table I, the lipid concentration is 200 mM, and all liposomes are composed of 80 mole percent egg phosphatidyl choline (EPC) and 20 mole percent cholesterol. Also, for each liposome and compound combination (e.g., Mn-EDTA-DDP liposomes) the liposomes comprise 33 mole percent of the compound (e.g. Mn-EDTA-DDP) and 67 mole percent lipid (8:2 EPC/cholesterol).

In Table I, R1 and R2 refer to 1/T1 and 1/T2 per millimole of paramagnetic ion per $sec^{-1}$, except for phosphate buffered saline (PBS), which refers to 1/T1 and 1/T2 for comparision.

Gd-DTPA, Mn-EDTA-MEA, Mn-EDTA-MEA liposomes, and PBS are all comparative examples. Gd-DTPA and Mn-EDTA-MEA are complexes without liposomes. Mn-EDTA-MEA liposomes refers to the complex entrapped within liposomes. For all others liposome examples, the respective complexes are incorporated into membranes of liposomes.

As Table I clearly illustrates, the contrast agents of the invention show high relaxivity.

EXAMPLE 18

Stability of Liposomal Mn-EDTA-ODP

Stability experiments were carried out with liposomal Mn-EDTA-ODP contrast agents of the invention, prepared in accordance with Example 8. To carry out the experiments, Mn-EDTA-ODP liposomes were placed within dialysis tubing with a 500 molecular weight cutoff (Sprectrum Medical, Los Angeles, Calif.) containing either PBS or PBS and 50% human serum. Dialysis tubing was suspended within a 500 ml beaker containing PBS which was placed into a shaking water bath maintained at 40° C. Two ml samples of each preparation were obtained from the dialysis tubing at 0, 12, and 24 hours. Samples were analyzed for $Mn^{+2}$ concentration by a spectrophotometric assay. PBS within the beakers was changed ever 8 hours.

The results are shown in Table II. The low level of change in each sample indicates a high stability of the contrast agents of the invention. The high serum stability, in particular, sets the contrast agents of the invention apart from many of the contrast agents known heretofor.

TABLE II

Serum stability of Mn-EDTA-ODP Liposomes Measured In Percentage Manganese Retained

| Liposome Diameter | Initial | 12 hours | 24 hours |
|---|---|---|---|
| 0.1 μ + PBS | 100 | 85.29 | 84.45 |
| 0.4 μ + PBS | 100 | 97.90 | 95.39 |
| 0.1 μ + 50% serum | 100 | 91.18 | 96.22 |
| 0.4 μ + 50% serum | 100 | 96.22 | 96.22 |

EXAMPLE 19

In Vitro Relaxivity of Mn-EDTA-DDP and Mn-EDTA-DDP Albumin Suspensions

Mn-EDTA-DDP and Mn-EDTA-DDP albumin suspensions (contrast agents within the scope of the invention) were prepared in accordance with Example 11, except that water instead of saline was used. The samples scanned by NMR using a 0.5 Tesla (21.3 MHz) Toshiba MRI scanner (Nasu, Japan) to determine relaxivity. The results were compared with similar scans for other compounds not within the scope of the invention. Specifically, scans were made of contrast agent of the invention, Mn-EDTA-DDP, Mn-EDTA-DDP albumin suspensions (both heated to 55° C., and unheated), and compared with scans of PBS, Gd-DTPA, $MnCl_2$, and $MnCl_2$ albumin suspensions. $MnCl_2$, and the $MnCl_2$ liposomes were prepared in accordance with Example 15.

The results are shown in Table III. Comparing the relaxivity of the albumin Mn-EDTA-DDP to the relaxivity of the Mn-EDTA-DDP alone, there is a significant improvement in relaxivity for the contrast agent with albumin. Not intending to be bound by any theory of operation, the improvement in relaxivity of Mn-EDTA-DDP with albumin is believed to result from albumin binding with the contrast agent. This binding is likely non-covalent and due to Van der Waals forces, representing an attraction between the acyl chains of the Mn-EDTA-DDP and the hydrophobic domains of the albumin molecule. The data also show that albumin with manganese causes no similar improvement in relaxivity, i.e., the relaxivity of manganese plus albumin is similar to manganese ion alone. Whether or not the albumin is heated appears to have little effect on the increase in relaxivity of Mn-EDTA-DDP.

TABLE III

In Vitro Relaxivity of Manganese and Mn-EDTA-DDP With and Without Albumin 0.5 Tesla

| Sample | R1 | R2 |
|---|---|---|
| Albumin w/$MnCl_2$ | 8.39 ± 0.446 | 34.18 ± 0.689 |
| Albumin Mn-EDTA-DDP | 24.6 ± 0.375 | 37.0 ± 1.21 |
| Mn-EDTA-DDP-Albumin (Heated to 55° C.) | 23.3 ± 0.593 | 34.1 ± 0.481 |
| MN-EDTA-DDP | 9.83 ± 0.332 | 15.20 ± 0.393 |
| $MnCl_2$ | 8.73 ± 0.928 | 39.45 ± 0.515 |
| Gd-DTPA 1.0 mM | 4.58 ± 0.143 | 5.41 ± 0.65 |

EXAMPLE 20

In Vivo Efficacy of Mn-EDTA-ODP and Mn-EDTA-DDP Liposomes

Mn-EDTA-ODP and Mn-EDTA-DDP liposomes of both 30 nm and 100 nm (contrast agents within the scope of the invention) were prepared in accordance with Example 8, injected intraveneously via a tail vein injection into rats bearing hepatic tumors (C5 clonal derivative epithelioid neoplasms), and the rats imaged using a 1.5 Tesla GE Signa Clinical Magnet equipped with a linear knee coil. Animals wre anesthesized with a 10:1 mixture v/v of ketamine (100 mg/ml) and acepoumozine (10 mg/ml) prior to imaging. Imaging parameters were: TR=250; TE=12; Matrix=256× 192; NEX=8; FOV 16 cm; Slice Thickness=3 mm; Slice Gap=1 mm. Images were taken in the coronal plane, mapped off an axial scout image. For comparision, rats were also injected with $MnCl_2$, and $MnCl_2$ liposomes, prepared in accordance with Example 15.

The results are shown in Tables IV A–D. The data for Mn-EDTA-ODP 30 nm liposomes is shown in Table IV A. As the data indicates, the Mn-EDTA-ODP liposomal contrast agents are highly effective. Also, as shown by Tables IV B, C and D, Mn-EDTA-DDP liposomes are much more effective than either free $MnCl_2$ or $MnCl_2$ liposomes. Hepatic enhancement was much more specific with the Mn-EDTA-DDP 100 nm liposomes than for either MnCl$_2$ or MnCl$_2$ liposomes.

TABLE IV A

In Vivo Efficacy of Mn-EDTA-ODP Liposomes (30 nm diameter)

| | ID | Rat 1 40 µmol/kg | Rat 2 100 µmol/kg | Rat 3 100 µmol/kg | Rat 4 200 µmol/kg |
|---|---|---|---|---|---|
| Pre | Liver & | 232 ± 26 | 218 ± 20 | 217 ± 23 | 172 ± 23 |
| | Muscle | 130 ± 22 | 110 ± 18 | 103 ± 24 | 103 ± 16 |
| | Noise | 27 ± 11 | 27 ± 11 | 37 ± 15 | 37 ± 15 |
| | S/N Ratio | | | | |
| | Liver & | 8.6 | 8.1 | 5.9 | 4.6 |
| | Muscle | 4.8 | 4.1 | 2.8 | 2.8 |
| Post | Liver & | 435 ± 57 | 447 ± 35 | 515 ± 52 | 329 ± 49 |
| | Muscle | 98 ± 16 | 141 ± 19 | 225 ± 18 | 200 ± 15 |
| | Noise | 23 ± 9 | 23 ± 9 | 29 ± 11 | 29 ± 11 |
| | S/N Ratio | | | | |
| | Liver & | 18.9 | 19.4 | 17.8 | 11.3 |
| | Muscle | 4.3 | 6.1 | 7.8 | 6.9 |

In Table IV A, imaging was preformed with one rat at each dose. S/N denotes signal to noise ratio.

TABLE IV B

In Vivo Efficacy of Mn-EDTA-DDP Liposomes Percent Liver Enhancement

| | MnCl$_2$ | | MnCl$_2$ Liposomes (100 nm diameter) | | Mn-EDTA-DDP Liposomes (100 nm) diameter) | |
|---|---|---|---|---|---|---|
| Dosage µM/kg | post | delayed post * | post | delayed post * | post | delayed post * |
| 0.5 | 0 | 0 | NA | NA | 26 | 26 |
| 1.0 | 0 | 0 | 18.3 | 18.9 | 34 | 31 |
| 2.5 | 25 | 29.4 | 36 | 43 | 44 | 42 |
| 5.0 | 43 | 21 | 62.4 | 53.2 | 88 | 86.5 |
| 10 | 81 | 61 | 84.1 | 74.2 | 100 | 92 |

In Table IV B, the "*" denotes a 30 minutes delay in imaging. Also, NA denotes that imaging was not done at the indicated dosage. The liposomes employed were composed of 80 mole percent egg phosphatidylcholine (EPC) and 20 mole percent cholesterol. With the Mn-EDTA-DDP liposomes, there was a 1:3 molar ratio of Mn-EDTA-DDP to lipid in the liposomes (lipid was 8:2 EPC/cholesterol). The data was obtained from one rat imaged at each dose.

TABLE IV C

In Vivo Efficacy of Mn-EDTA-DDP Liposome Tumor Contrast to Noise

| Dosage | MnCl$_2$ | | MnCl$_2$ Liposomes | | Mn-EDTA-DDP Liposomes (100 nm diameter) | |
|---|---|---|---|---|---|---|
| µM/kg | pre | post | pre | post | pre | post |
| 0.5 | 28 | 19 | NA | NA | 28 | 38.3 |
| 1.0 | 37.5 | 23 | NT | NT | 21 | 29.4 |
| 2.5 | 13.1 | 17.9 | 35.5 | 51.5 | 12.5 | 67 |

TABLE IV C-continued

In Vivo Efficacy of Mn-EDTA-DDP Liposome Tumor Contrast to Noise

| Dosage | MnCl$_2$ | | MnCl$_2$ Liposomes | | Mn-EDTA-DDP Liposomes (100 nm diameter) | |
|---|---|---|---|---|---|---|
| µM/kg | pre | post | pre | post | pre | post |
| 5.0 | 21.3 | 28.3 | 26.5 | 73.0 | NT | NT |
| 10.0 | 9.3 | 29.2 | 27.5 | 80.0 | 7.8 | 56 |

In Table IV C, NT denotes that no tumors were detected, and NA denotes that imaging not done at the indicated dosage.

TABLE IV D

In Vivo Efficacy of Mn-EDTA-DDP Liposomes Tumor Contrast To Noise (30 minute delay)

| Dosage µM/kg | MnCl$_2$ | MnCl$_2$ Liposomes (100 nm diameter) | Mn-EDTA-DDP Liposomes (100 nm diameter) |
|---|---|---|---|
| 0.5 | 12 | NA | 49.2 |
| 1.0 | 16 | NT | 37.6 |
| 2.5 | 35.9 | 40 | 50 |
| 5.0 | 31.3 | 62.0 | NT |
| 10.0 | 29.6 | 60.0 | 59 |

In Table IV D, NT denotes that no tumors were detected, and NA denotes that imaging not done at the indicated dosage.

EXAMPLE 21

In Vivo Toxicity of Mn-EDTA-DDP and Mn-EDTA-DDP Liposomes

Outbred ICR mice (Harlan Sprague Dawley, Indianapolis, Ind.) were injected intravenously via a tail vein injection with various doses of Mn-EDTA-DDP and Mn-EDTA-DDP liposomes, prepared in accordance with Example 8, and the LD50 measured. As a comparision, the mice were also injected with MnCl$_2$ and MnCl$_2$ liposomes.

The results are shown in Table V. As Table V reveals, liposomes bearing Mn-EDTA-DDP are the least toxic of any of the compounds tested. Using Mn-EDTA-DDP liposomes, the LD50 was greater than 1,062 micromoles of manganese per kg. This confers a therapeutic index of more than 400:1, asssuming an imaging dose of 2.5 µmol/kg (more than adequate for improving liver to tumor contrast). At a dose of 1062 µmol/kg, Mn-EDTA-DDP liposomes all mice survived and had similar activity scores as mice receiving normal saline.

TABLE V

In Vivo Toxicity Testing

| Agent | Interpolated LD50s (µmole/kg) |
|---|---|
| MnCl$_2$ | 250 |
| MnCl$_2$ Liposomes | 700 |
| Mn-EDTA-DDP | 240 |
| Mn-EDTA-DDP in Liposomes | >1062 |

In Table V, liposomes denotes manganese chloride salt entrapped in 100 nm diameter liposomes comprised of 8:2

EPC/cholesterol. Also, Mn-EDTA-DDP in liposomes refers to 100 nm liposomes comprised of 1:3 Mn-EDTA-DDP to lipid (where the lipid is 8:2 EPC/cholesterol).

What is claimed is:

1. A contrast agent for magnetic resonance imaging comprising a paramagnetic ion in combination with a compound of the formula $$R_2R_1N-\underset{\underset{O}{\parallel}}{C}-CH_2-\underset{\underset{(CH_2CH_2-N)_{\overline{n}}-(CH_2)_mCH_2}{|}}{N}\underset{CH_2COOH}{\overset{CH_2-(CH_2)_{\overline{m}}-N-CH_2-CH_2}{|}}\underset{CH_2COOH}{|}N-CH_2-\underset{\underset{O}{\parallel}}{C}-NR_1R_2 \quad (III)$$

wherein:
each $R_1$ is, independently, a substituted or unsubstituted $C_7$–$C_{30}$ straight chain or cyclic compound;
each $R_2$ is, independently, a substituted or unsubstituted $C_1$–$C_{30}$ straight chain or cyclic compound which may be internally interrupted by O, NH, $NR_3$, or S, where $R_3$ is a $C_1$–$C_3$ alkyl;
each m is 1 to 2; and
n is 1 to 20.

2. A contrast agent of claim 1 wherein $R_1$ is an unsubstituted $C_7$–$C_{30}$ alkyl.

3. A contrast agent of claim 2 wherein $R_1$ is an unsubstituted $C_8$–$C_{18}$ alkyl.

4. A contrast agent of claim 1 wherein at least one of said $R_2$ groups is a substituted or unsubstituted $C_1$–$C_{30}$ straight chain or cyclic compound which is internally interrupted by O, NH, $NR_3$ or S.

5. A contrast agent of claim 4 wherein at least one of said $R_2$ groups is a substituted or unsubstituted $C_2$–$C_{12}$ straight chain or cyclic compound which is internally interrupted by O, NH, $NR_3$ or S.

6. A contrast agent of claim 1 wherein n is 1 to 2.

7. A contrast agent of claim 1 wherein $R_1$ is octadecyl, $R_2$ is 2,3-dihydroxypropyl, m is 1, and n is 1.

8. A contrast agent of claim 1 wherein the paramagnetic ion comprises an ion selected from the group consisting of $Cr^{+3}$, $Co^{+2}$, $Mn^{+2}$, $Ni^{+2}$, $Fe^{+3}$, $Fe^{+2}$, $La^{+3}$, $Cu^{+2}$, $Gd^{+3}$, $Ce^{+3}$, $Tb^{+3}$, $Pr^{+3}$, $Dy^{+3}$, $Nd^{+3}$, $Ho^{+3}$, $Pm^{+3}$, $Er^{+3}$, $Sm^{+3}$, $Tm^{+3}$, $Eu^{+3}$, $Yb^{+3}$ and $Lu^{+3}$.

9. A contrast agent of claim 8 wherein the paramagnetic ion comprises an ion selected from the group consisting of $Mn^{+2}$, $Fe^{+3}$ and $Gd^{+3}$.

10. A contrast agent of claim 9 wherein the paramagnetic ion is $Mn^{+2}$.

11. A contrast agent of claim 7 wherein the paramagnetic ion is $Mn^{+2}$.

12. A contrast agent of claim 1 further comprising a lipid compound.

13. A contrast agent of claim 12 wherein the lipid compound comprises a lipid selected from the group consisting of cholesterols, phosphatidylcholines, phosphatidylethanolamines, phosphatidylserines, phosphatidylglycerols, phosphatidic acids, phosphatidylinositols, phospholipids, lysolipids, fatty acids, sphingomyelin, glycosphingolipids, glucolipids, glycolipids, sulphatides, lipids with ether and ester-linked fatty acids and polymerizable lipids.

14. A contrast agent of claim 12 wherein the lipid compound is in the form of a lipid emulsion, liposome, or micelle, or a combination thereof.

15. A contrast agent of claim 1 further comprising a suspending agent.

16. A contrast agent of claim 15 wherein the suspending agent comprises a suspending agent selected from the group consisting of polyethylene glycol, lactose, mannitol, sorbitol, ethyl alcohol, glycerin, lecithin, polyoxyethylene sorbitan monoleate, sorbitan monoleate and albumin.

17. A method of providing an image of an internal region of a patient comprising (i) administering to the patient a contrast agent of claim 1, and (ii) scanning the patient using magnetic resonance imaging to obtain visible images of the region.

18. A method for diagnosing the presence of diseased tissue in a patient comprising (i) administering to the patient a contrast agent of claim 1, and (ii) scanning the patient using magnetic resonance imaging to obtain visible images of any diseased tissue in the patient.

19. A contrast agent of claim 5 wherein at least one of said $R_2$ groups is a substituted or unsubstituted $C_2$–$C_6$ straight chain or cyclic compound which is internally interrupted by O, NH, $NR_3$ or S.

20. A contrast agent of claim 19 wherein at least one of said $R_2$ groups is a substituted or unsubstituted $C_2$–$C_6$ alkyl group which is internally interrupted by O, NH, $NR_3$ or S.

21. A contrast agent of claim 20 wherein at least one of said $R_2$ groups is a substituted or unsubstituted $C_2$–$C_6$ alkyl group which is internally interrupted by O.

22. A contrast agent of claim 21 wherein at least one of said $R_2$ groups is unsubstituted.

23. A contrast agent of claim 1 wherein each of said $R_2$ groups is, independently, a substituted or unsubstituted $C_1$–$C_{30}$ straight chain or cyclic compound which is internally interrupted by O, NH, $NR_3$ or S.

24. A contrast agent of claim 23 wherein each of said $R_2$ groups is, independently, a substituted or unsubstituted $C_2$–$C_{12}$ straight chain or cyclic compound which is internally interrupted by O, NH, $NR_3$ or S.

25. A contrast agent of claim 24 wherein each of said $R_2$ groups is, independently, a substituted or unsubstituted $C_2$–$C_6$ straight chain or cyclic compound which is internally interrupted by O, NH, $NR_3$ or S.

26. A contrast agent of claim 25 wherein each of said $R_2$ groups is, independently, a substituted or unsubstituted $C_2$–$C_6$ alkyl group which is internally interrupted by O, NH, $NR_3$ or S.

27. A contrast agent of claim 26 wherein each of said $R_2$ groups is, independently, a substituted or unsubstituted $C_2$–$C_6$ alkyl group which is internally interrupted by O.

28. A contrast agent of claim 27 wherein each of said $R_2$ groups is unsubstituted.

29. A contrast agent of claim 1 wherein at least one of said $R_2$ groups is uninterrupted.

30. A contrast agent of claim 29 wherein at least one of said $R_2$ groups is a substituted or unsubstituted uninterrupted $C_2$–$C_{12}$ straight chain or cyclic compound.

31. A contrast agent of claim 30 wherein at least one of said $R_2$ groups is a substituted or unsubstituted uninterrupted $C_2$–$C_6$ straight chain or cyclic compound.

32. A contrast agent of claim 31 wherein at least one of said $R_2$ groups is a substituted or unsubstituted uninterrupted $C_2$–$C_6$ alkyl group.

33. A contrast agent of claim 32 wherein at least one of said $R_2$ groups is a substituted or unsubstituted uninterrupted $C_2$–$C_6$ alkyl group.

34. A contrast agent of claim 33 wherein at least one of said $R_2$ groups is an uninterrupted $C_2$–$C_6$ alkyl group substituted with OH.

35. A contrast agent of claim 1 wherein:
at least one of said $R_2$ groups is $-CH_2(CHOH)_nCH_2OR_4$, $-CH_2-(CH_2)_m-X-R_4$, $-(CH_2CH_2X)_mR_4$ or $-(CHOH)_m-OR_4$;
X is O, NH, $NR_3$ or S, where $R_3$ is $C_1-C_3$ alkyl;
$R_4$ is $-(CH_2)_m-CH_3$; and
each m is independently an integer from 0 to about 26.

36. A contrast agent of claim 35 wherein each of said $R_2$ groups is $-CH_2(CHOH)_nCH_2OR_4$, $-CH_2-(CH_2)_m-X-R_4$, $-(CH_2CH_2X)_mR_4$ or $-(CHOH)_m-OR_4$.

37. A contrast agent of claim 36 wherein X is O.

38. A contrast agent for magnetic resonance imaging comprising a paramagnetic ion in combination with a compound of the formula

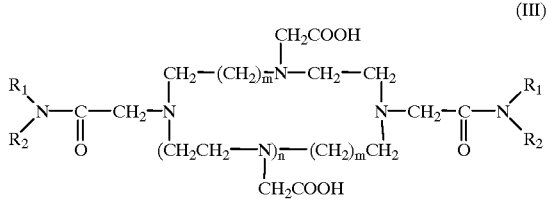

(III)

wherein:
each $R_1$ is, independently, a substituted or unsubstituted $C_7-C_{30}$ straight chain or cyclic compound;
each $R_2$ is a polyethylene glycol substituent or a substituted or unsubstituted $C_1-C_{30}$ straight chain or cyclic compound which may be internally interrupted by O, NH, $NR_3$ or S;
$R_3$ is $C_1-C_3$ alkyl;
each m is 1 to 2; and
n is 1 to 20;
provided that at least one of $R_2$ is a polyethylene glycol substituent.

39. A contrast agent of claim 38 wherein each $R_2$ is independently a polyethylene glycol substituent.

40. A contrast agent for magnetic resonance imaging comprising, in combination with a paramagnetic ion and a lipid compound, a compound of the formula

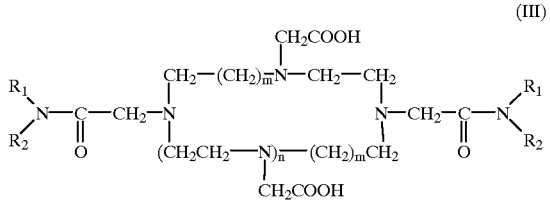

(III)

wherein:
each $R_1$ is, independently, a substituted or unsubstituted $C_7-C_{30}$ straight chain or cyclic compound;
each $R_2$ is, independently, a substituted or unsubstituted $C_1-C_{30}$ straight chain or cyclic compound which may be internally interrupted by O, NH, $NR_3$ or S, where $R_3$ is $C_1-C_3$ alkyl;
each m is 1 to 2; and
n is 1 to 20.

41. A contrast agent of claim 40 wherein the lipid compound is selected from the group consisting of cholesterols, phosphatidylcholines, phosphatidylethanolamines, phosphatidylserines, phosphatidylglycerols, phosphatidic acids, phosphatidylinositols, phospholipids, lysolipids, fatty acids, sphingomyelin, glycosphingolipids, glucolipids, glycolipids, sulphatides, lipids with ether and ester-linked fatty acids and polymerizable lipids.

42. A contrast agent of claim 41 wherein the lipid compound is in the form of a lipid emulsion, liposome or micelle, or a combination thereof.

43. A contrast agent for magnetic resonance imaging comprising, in combination with a paramagnetic ion and a suspending agent, a compound of the formula

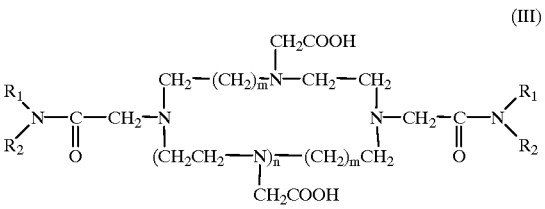

(III)

wherein:
each $R_1$ is, independently, a substituted or unsubstituted $C_7-C_{30}$ straight chain or cyclic compound;
each $R_2$ is, independently, a substituted or unsubstituted $C_1-C_{30}$ straight chain or cyclic compound which may be internally interrupted by O, NH, $NR_3$ or S, where $R_3$ is $C_1-C_3$ alkyl;
each m is 1 to 2; and
n is 1 to 20.

44. A contrast agent of claim 43 wherein the suspending agent is selected from the group consisting of polyethylene glycol, lactose, mannitol, sorbitol, ethyl alcohol, glycerin, lecithin, polyoxyethylene sorbitan monoleate, sorbitan monoleate and albumin.

45. A compound of the formula

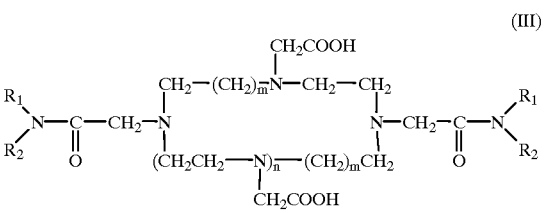

(III)

wherein:
each $R_1$ is, independently, a substituted or unsubstituted $C_7-C_{30}$ straight chain or cyclic compound;
each $R_2$ is, independently, a substituted or unsubstituted $C_1-C_{30}$ straight chain or cyclic compound which may be internally interrupted by O, NH, $NR_3$ or S, where $R_3$ is $C_1-C_3$ alkyl;
each m is 1 to 2; and
n is 1 to 20.

46. A compound of claim 45 wherein $R_1$ is an unsubstituted $C_7-C_{30}$ alkyl.

47. A compound of claim 46 wherein $R_1$ is an unsubstituted $C_8-C_{18}$ alkyl.

48. A compound of claim 45 wherein at least one of said $R_2$ groups is a substituted or unsubstituted $C_1-C_{30}$ straight chain or cyclic compound which is internally interrupted by O, NH, $NR_3$ or S.

49. A compound of claim 48 wherein at least one of said $R_2$ groups is a substituted or unsubstituted $C_2-C_{12}$ straight chain or cyclic compound which is internally interrupted by O, NH, $NR_3$ or S.

50. A compound of claim 49 wherein at least one of said $R_2$ groups is a substituted or unsubstituted $C_2$–$C_6$ straight chain or cyclic compound which is internally interrupted by O, NH, $NR_3$ or S.

51. A compound of claim 50 wherein at least one of said $R_2$ groups is a substituted or unsubstituted $C_2$–$C_6$ alkyl group which is internally interrupted by O, NH, $NR_3$ or S.

52. A compound of claim 51 wherein at least one of said $R_2$ groups is a substituted or unsubstituted $C_2$–$C_6$ alkyl group which is internally interrupted by O.

53. A compound of claim 52 wherein at least one of said $R_2$ groups is unsubstituted.

54. A compound of claim 45 wherein each of said $R_2$ groups is, independently, a substituted or unsubstituted $C_1$–$C_{30}$ straight chain or cyclic compound which is internally interrupted by O, NH, $NR_3$ or S.

55. A compound of claim 54 wherein each of said $R_2$ groups is, independently, a substituted or unsubstituted $C_2$–$C_{12}$ straight chain or cyclic compound which is internally interrupted by O, NH, $NR_3$ or S.

56. A compound of claim 55 wherein each of said $R_2$ groups is, independently, a substituted or unsubstituted $C_2$–$C_6$ straight chain or cyclic compound which is internally interrupted by O, NH, $NR_3$ or S.

57. A compound of claim 56 wherein each of said $R_2$ groups is, independently, a substituted or unsubstituted $C_2$–$C_6$ alkyl group which is internally interrupted by O, NH, $NR_3$ or S.

58. A compound of claim 57 wherein each of said $R_2$ groups is, independently, a substituted or unsubstituted $C_2$–$C_6$ alkyl group which is internally interrupted by O.

59. A compound of claim 58 wherein each of said $R_2$ groups is unsubstituted.

60. A compound of claim 45 wherein at least one of said $R_2$ groups is uninterrupted.

61. A compound of claim 60 wherein at least one of said $R_2$ groups is a substituted or unsubstituted uninterrupted $C_2$–$C_{12}$ straight chain or cyclic compound.

62. A compound of claim 61 wherein at least one of said $R_2$ groups is a substituted or unsubstituted uninterrupted $C_2$–$C_6$ straight chain or cyclic compound.

63. A compound of claim 62 wherein at least one of said $R_2$ groups is a substituted or unsubstituted uninterrupted $C_2$–$C_6$ alkyl group.

64. A compound of claim 63 wherein at least one of said $R_2$ groups is a substituted or unsubstituted uninterrupted $C_2$–$C_6$ alkyl group.

65. A compound of claim 64 wherein said substituent is OH.

66. A compound of claim 45 wherein:
at least one of said $R_2$ groups is —$CH_2(CHOH)_nCH_2OR_4$, —$CH_2$—$(CH_2)_m$—X—$R_4$, —$(CH_2CH_2X)_mR_4$ or —$(CHOH)_m$—$OR_4$;
X is O, NH, $NR_3$ or S, where $R_3$ is $C_1$–$C_3$ alkyl;
$R_4$ is —$(CH_2)_m$—$CH_3$; and
each m is independently an integer from 0 to about 26.

67. A compound of claim 66 wherein each of said $R_2$ groups is —$CH_2(CHOH)_nCH_2OR_4$, —$CH_2$—$(CH_2)_m$—X—$R_4$, —$(CH_2CH_2X)_mR_4$ or —$(CHOH)_m$—$OR_4$.

68. A compound of claim 67 wherein X is O.

69. A compound of the formula

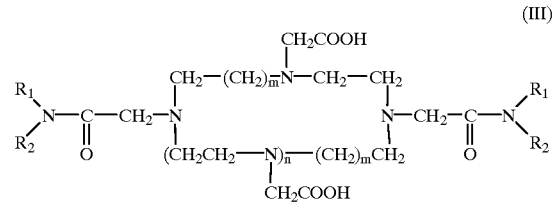

wherein:
each $R_1$ is, independently, a substituted or unsubstituted $C_7$–$C_{30}$ straight chain or cyclic compound;
each $R_2$ is a polyethylene glycol substituent or a substituted or unsubstituted $C_1$–$C_{30}$ straight chain or cyclic compound which may be internally interrupted by O, NH, $NR_3$ or S;
$R_3$ is $C_1$–$C_3$ alkyl;
each m is 1 to 2; and
n is 1 to 20;
provided that at least one of $R_2$ is a polyethylene glycol substituent.

70. A compound of claim 69 wherein each $R_2$ is independently a polyethylene glycol substituent.

* * * * *

UNITED STATES PATENT AND TRADEMARK OFFICE
CERTIFICATE OF CORRECTION

PATENT NO.   : 6,010,682                                         Page 1 of 2
DATED        : January 4, 2000
INVENTOR(S)  : Evan C. Unger and DeKang Shen It is certified that error appears in the above-identified patent and that said Letters Patent is hereby corrected as shown below:

Title page,
Item [56], OTHER PUBLICATIONS, at Andress, Jr., second line thereof, please delete "chemistry" and insert -- Chemistry -- therefor.

Column 3,
Line 23, please delete "alky" and insert -- alkyl -- therefor.

Column 9,
Line 27, please delete "singlely" and insert -- singly -- therefor.
Line 65, please delete "phosphalidycholine" and insert -- phosphatidylcholine -- therefor.

Column 10,
Line 15, please insert a -- . -- after "ceramides".

Column 11,
Line 44, please delete "dibutroyl" and insert -- dibutyroyl -- therefor.

Column 13,
Line 10, please delete "whch" and insert -- which -- therefor.

Column 14,
Line 54, please delete "example" and insert -- examples -- therefor.

Column 16,
Line 53, please delete "ref luxed" and insert -- refluxed -- therefor.

Column 25,
Lines 27-42, please delete the structure

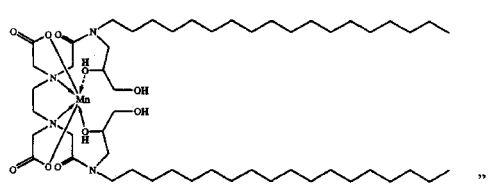

and insert the structure

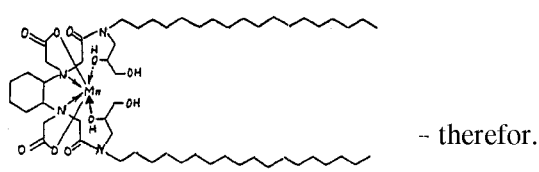

-- therefor.

UNITED STATES PATENT AND TRADEMARK OFFICE
CERTIFICATE OF CORRECTION

PATENT NO.   : 6,010,682
DATED        : January 4, 2000
INVENTOR(S)  : Evan C. Unger and DeKang Shen It is certified that error appears in the above-identified patent and that said Letters Patent is hereby corrected as shown below:

Column 25,
Line 60, please delete "Octadecylamidonlethyl" and insert -- Octadecylamidomethyl -- therefor.

Column 27,
Line 45, please delete "ever" and insert -- every -- therefor.

Column 30,
Line 50, please delete "asssuming" and insert -- assuming -- therefor.
Line 66, please delete "Table V, liposomes" and insert -- Table V, MnCl$_2$ liposomes -- therefor.

Signed and Sealed this

Sixteenth Day of July, 2002

Attest:

JAMES E. ROGAN
Attesting Officer      Director of the United States Patent and Trademark Office